United States Patent
Josse et al.

(10) Patent No.: US 12,303,121 B2
(45) Date of Patent: May 20, 2025

(54) SURGICAL SYSTEM AND METHOD

(71) Applicant: Warsaw Orthopedic, Inc., Warsaw, IN (US)

(72) Inventors: Loïc Josse, Palm Beach Garden, FL (US); Bertrand Peultier, Les Hopitaux Neufs (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 473 days.

(21) Appl. No.: 17/605,819

(22) PCT Filed: Apr. 23, 2019

(86) PCT No.: PCT/US2019/028615
§ 371 (c)(1),
(2) Date: Oct. 22, 2021

(87) PCT Pub. No.: WO2020/219016
PCT Pub. Date: Oct. 29, 2020

(65) Prior Publication Data
US 2022/0202405 A1    Jun. 30, 2022

(51) Int. Cl.
*A61B 17/02*    (2006.01)
*A61B 17/00*    (2006.01)

(52) U.S. Cl.
CPC .. *A61B 17/025* (2013.01); *A61B 2017/00057* (2013.01); *A61B 2017/0256* (2013.01)

(58) Field of Classification Search
CPC .......... A61B 17/02; A61B 17/025; A61B 1/32
See application file for complete search history.

(56) References Cited

U.S. PATENT DOCUMENTS

| 6,030,402 A | 2/2000 | Thompson et al. |
| 6,139,493 A | 10/2000 | Koros et al. |
| 8,974,497 B2 | 3/2015 | Cho et al. |
| 9,402,660 B2 | 8/2016 | Brinkman et al. |

(Continued)

FOREIGN PATENT DOCUMENTS

| CN | 101489497 | 7/2009 |
| CN | 108498152 | 9/2018 |

(Continued)

OTHER PUBLICATIONS

International Search Report for PCT/US2019/028615 date of completion is Feb. 21, 2020 (2 pages).

(Continued)

*Primary Examiner* — Christopher J Beccia
(74) *Attorney, Agent, or Firm* — Sheridan Ross P.C.

(57) ABSTRACT

A surgical instrument includes a first member including a first portion and a second portion. The second portion includes an arm and a part. The part is connectable with a first blade such that the first blade is rotatable about the longitudinal axis through a selected angular range and about the transverse axis through a selected angular range. A second member includes a first portion and a second portion that is connectable with a second blade. The first portions are pivotably connected such that the blades are movable between a first configuration and a second configuration to define an opening and space tissue adjacent a spine. Surgical systems, constructs, implants and methods are disclosed.

19 Claims, 39 Drawing Sheets

(56) References Cited

U.S. PATENT DOCUMENTS

| | | | |
|---|---|---|---|
| 10,314,620 B2 | 6/2019 | Cho et al. | |
| 2006/0084844 A1 | 4/2006 | Nehls | |
| 2007/0208227 A1* | 9/2007 | Smith | A61B 1/313 600/219 |
| 2008/0140129 A1 | 6/2008 | Dalton | |
| 2010/0069976 A1 | 3/2010 | de Villiers et al. | |
| 2012/0296172 A1* | 11/2012 | Raven, III | A61B 17/0206 600/231 |
| 2012/0316609 A1 | 12/2012 | Wall et al. | |
| 2013/0310942 A1 | 11/2013 | Abdou | |
| 2014/0024900 A1 | 1/2014 | Capote et al. | |
| 2014/0066718 A1* | 3/2014 | Fiechter | A61B 17/0206 600/214 |
| 2014/0107656 A1 | 4/2014 | Masson et al. | |
| 2014/0257044 A1 | 9/2014 | Blain et al. | |
| 2014/0257312 A1 | 9/2014 | Solitario, Jr. et al. | |
| 2014/0350347 A1* | 11/2014 | Karpowicz | A61F 2/4455 600/215 |
| 2015/0045834 A1 | 2/2015 | McBride | |
| 2015/0164569 A1* | 6/2015 | Reitblat | A61B 17/7077 606/279 |
| 2015/0351738 A1 | 12/2015 | Perrow | |
| 2016/0074029 A1 | 3/2016 | O'Connell et al. | |
| 2016/0089188 A1 | 3/2016 | McBride, Jr. et al. | |
| 2016/0206442 A1 | 7/2016 | Dvorak et al. | |
| 2016/0345952 A1 | 12/2016 | Kucharzyk et al. | |
| 2017/0035406 A1 | 2/2017 | Abidin et al. | |
| 2017/0100116 A1 | 4/2017 | Erramilli et al. | |
| 2017/0112539 A1 | 4/2017 | Hayes | |
| 2017/0119449 A1 | 5/2017 | Jones et al. | |
| 2017/0215856 A1 | 8/2017 | Martinelli et al. | |
| 2017/0252107 A1 | 9/2017 | Jones et al. | |
| 2017/0258502 A1 | 9/2017 | Abdou | |
| 2017/0311985 A1 | 11/2017 | Bobbitt et al. | |
| 2018/0042594 A1 | 2/2018 | Miles et al. | |
| 2018/0161101 A1 | 6/2018 | Barsoum et al. | |
| 2018/0289363 A1 | 10/2018 | Barnes et al. | |
| 2018/0303473 A1 | 10/2018 | Spann et al. | |
| 2018/0303552 A1 | 10/2018 | Ryan et al. | |
| 2019/0021716 A1 | 1/2019 | Waugh et al. | |
| 2019/0046239 A1 | 2/2019 | Bobbitt et al. | |
| 2019/0069956 A1 | 3/2019 | Ryan et al. | |
| 2019/0090864 A1 | 3/2019 | Medeiros et al. | |
| 2019/0090979 A1 | 3/2019 | Medeiros et al. | |
| 2019/0110785 A1* | 4/2019 | Serokosz | A61B 17/0206 |
| 2019/0216453 A1 | 7/2019 | Predick et al. | |
| 2019/0223854 A1 | 7/2019 | Baudouin et al. | |
| 2020/0054361 A1 | 2/2020 | Peultier et al. | |
| 2022/0192645 A1 | 6/2022 | Peultier et al. | |
| 2022/0192647 A1 | 6/2022 | Josse et al. | |
| 2022/0202450 A1 | 6/2022 | Josse et al. | |
| 2022/0218417 A1 | 7/2022 | Josse et al. | |
| 2023/0059813 A1 | 2/2023 | Josse et al. | |

FOREIGN PATENT DOCUMENTS

| | | |
|---|---|---|
| CN | 110381866 | 10/2019 |
| EP | 3331421 | 6/2018 |
| EP | 3351185 | 7/2018 |
| GB | 2528416 | 1/2016 |
| KR | 10-1446620 B1 | 10/2014 |
| WO | WO 90/02527 | 3/1990 |
| WO | WO 2007/087536 | 8/2007 |
| WO | WO 2018/150214 | 8/2018 |
| WO | WO 2018/150215 | 8/2018 |
| WO | WO 2020/219016 | 10/2020 |
| WO | WO 2020/219018 | 10/2020 |
| WO | WO 2020/219019 | 10/2020 |
| WO | WO 2020/219020 | 10/2020 |
| WO | WO 2021/206723 | 10/2020 |

OTHER PUBLICATIONS

European Patent Office, 80298 Munich, Germany, Application No./Patent No. 199261 19.9, Extended European Search Report, Dated: Nov. 3, 2022.
China Office Action: China National Intellectual Property Administration: Search Report: Application/Patent No. 201980095607.3, Jan. 25, 2024.
Official Action for China Patent Application No. 202080099220.8, dated Nov. 8, 2024, 10 pages.
Official Action for U.S. Appl. No. 17/795,152, dated Nov. 26, 2024, 9 pages.
Notice of Allowance for U.S. Appl. No. 17/606,011, dated Dec. 5, 2024, 8 pages.
International Search Report and Written Opinion for International (PCT) Patent Application No. PCT/US2019/028612, dated Feb. 21, 2020, 7 pages.
International Preliminary Report on Patentability for International (PCT) Patent Application No. PCT/US2019/028612, dated Sep. 28, 2021, 6 pages.
Extended European Search Report for Europe Patent Application No. 19925665.2, dated Nov. 4, 2022, 10 pages.
International Search Report and Written Opinion for International (PCT) Patent Application No. PCT/US2019/028632, dated Feb. 21, 2020, 7 pages.
International Preliminary Report on Patentability for International (PCT) Patent Application No. PCT/US2019/028632, dated Sep. 28, 2021, 6 pages.
Extended European Search Report for Europe Patent Application No. 19925589.4, dated Nov. 7, 2022, 12 pages.
Official Action for China Patent Application No. 201980095623.2, dated Jan. 23, 2024, 2 pages.
Official Action for U.S. Appl. No. 17/606,013, dated Sep. 15, 2023, 5 pages. Restriction Requirement.
Official Action for U.S. Appl. No. 17/606,013, dated Mar. 21, 2024, 25 pages.
Official Action for U.S. Appl. No. 17/606,013, dated Jun. 12, 2024, 26 pages.
International Preliminary Report on Patentability for International (PCT) Patent Application No. PCT/US2019/028615, dated Feb. 21, 2020, 7 pages.
International Search Report and Written Opinion for International (PCT) Patent Application No. PCT/US2019/028624, dated Feb. 21, 2020, 9 pages.
International Preliminary Report on Patentability for International (PCT) Patent Application No. PCT/US2019/028624, dated Sep. 28, 2021 7 pages.
Extended European Search Report for Europe Patent Application No. 19925802.1, dated Nov. 8, 2022 10 pages.
Official Action for Europe Patent Application No. 19925802.1, dated Jul. 18, 2024, 3 pages.
International Search Report and Written Opinion for International (PCT) Patent Application No. PCT/US2019/028628, dated Feb. 21, 2020, 7 pages.
International Preliminary Report on Patentability for International (PCT) Patent Application No. PCT/US2019/028628, dated Sep. 28, 2021, 6 pages.
Extended European Search Report for Europe Patent Application No. 19925884.9, dated Nov. 8, 2022, 11 pages.
Official Action for China Patent Application No. 201980095615.8, dated Jan. 23, 2024, 2 pages.
International Search Report and Written Opinion for International (PCT) Patent Application No. PCT/US2020/027533, dated Jul. 6, 2020, 8 pages.
International Preliminary Report on Patentability for International (PCT) Patent Application No. PCT/US2020/027533, dated Oct. 6, 2022, 7 pages.
Extended European Search Report for Europe Patent Application No. 20930065.6, dated Mar. 13, 2024, 5 pages.
Official Action for U.S. Appl. No. 17/606,010, dated Dec. 20, 2023, 16 pages.
Notice of Allowance for U.S. Appl. No. 17/606,010, dated Jul. 9, 2024, 5 pages.

(56) References Cited

OTHER PUBLICATIONS

Corrected Notice of Allowance for U.S. Appl. No. 17/606,010, dated Jul. 29, 2024, 2 pages.
Notice of Allowance for U.S. Appl. No. 17/606,010, dated Sep. 16, 2024, 5 pages.
Official Action for U.S. Appl. No. 17/606,011, dated Jan. 18, 2024, 9 pages.
Official Action for U.S. Appl. No. 17/606,011, dated Jul. 3, 2024, 11 pages.

* cited by examiner

SURGICAL SYSTEM AND METHOD

CROSS-REFERENCE TO RELATED APPLICATIONS

This application is a National Stage Application of PCT/US2019/028615 filed Apr. 23, 2019, and the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis, and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical instrument is provided. The surgical instrument includes a first member including a first portion and a second portion. The second portion includes an arm defining a longitudinal axis and a part defining a transverse axis. The part is connectable with a first blade such that the first blade is rotatable about the longitudinal axis through a selected angular range and about the transverse axis through a selected angular range. A second member includes a first portion and a second portion that is connectable with a second blade. The first portions are pivotably connected such that the blades are movable between a first configuration and a second configuration to define an opening and space tissue adjacent a spine. In some embodiments, surgical systems, constructs, implants and methods are disclosed.

In one embodiment, a surgical system is provided. The surgical system includes a first member including a first portion and a second portion. The second portion includes an arm defining a longitudinal axis and a part defining a transverse axis. The part is connectable with a first blade such that the first blade is rotatable about the longitudinal axis through a selected angular range and about the transverse axis through a selected angular range. A second member includes a first portion and a second portion that is connectable with a second blade. The second portion of the second member includes an arm defining a longitudinal axis and a part defining a transverse axis. The part of the second member is connectable with the second blade such that the second blade is rotatable about the longitudinal axis of the second member through a selected angular range and about the transverse axis of the second member through a selected angular range. The first portions are pivotably connected such that the blades are movable between a first configuration and a second configuration to define an opening and space tissue adjacent a spine.

In one embodiment, a method for treating a spine is provided. The method comprises the steps of: engaging a first implant support with a first fastener having a shaft fixed with a spine; engaging a second implant support with a second fastener having a shaft fixed with the spine, the implant support being connected with a first surgical instrument to distract and/or compress the spine; disposing the first implant support relative to the second implant support in an axial orientation relative to the spine to define at least a portion of an opening and space tissue adjacent the spine; and moving a first member of a second surgical instrument relative to a second member of the second surgical instrument in a medial orientation relative to the spine to define at least a portion of the opening and space tissue adjacent the spine.

BRIEF DESCRIPTION OF THE DRAWINGS

The present disclosure will become more readily apparent from the specific description accompanied by the following drawings, in which.

DETAILED DESCRIPTION

Figure 1:
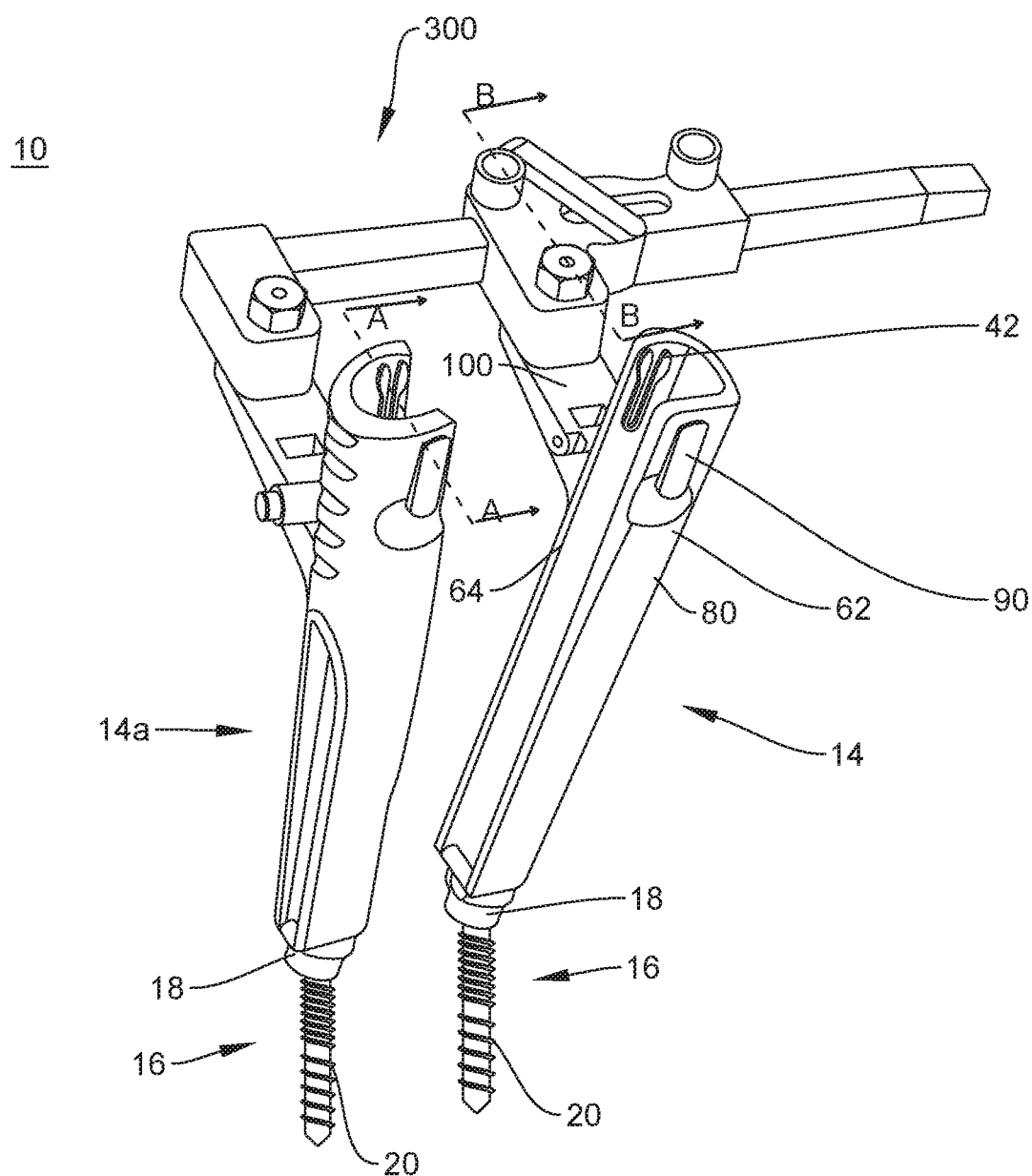
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a surgical trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal-adjusting screw (SAS), a fixed-axis screw (FAS) and/or a multi-axial screw (MAS). In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical instrument connected with an adaptor, which is utilized with a bone screw having extender tabs attached thereto. In some embodiments, the present surgical system includes an implant support including a connector and an adaptor. In some embodiments, the connector includes an outer sleeve configured for connection with extenders. In some embodiments, the connector is connected with extenders for insertion of an implant, such as for example, a spinal rod. In some embodiments, the adaptor includes an arm having a pivot hinge that connects the connector with a compressor/retractor. In some embodiments, the pivot hinge allows movement of the components to provide surgical-site visibility for inter-operative imaging. In some embodiments, a compressor/distractor is utilized for generally parallel distraction. In some embodiments, a compressor/distractor is utilized for generally parallel compression. In some embodiments, the surgical instrument includes a compressor/distractor having a reversible ratchet with a neutral, freely moveable position. In some embodiments, the present surgical system is employed with a procedure for implantation of a bone fastener percutaneously.

In some embodiments, the present surgical system includes a surgical instrument employed with a surgical method including the step of: pre-assembly of the distractor; pre-loading of the alignment guides; preparing for implantation of screws; connecting screw tabs; removal of the alignment guides; attaching a compressor/retractor having an articulating rack for segmental distraction; implanting an interbody and decompressing tissue, inserting a rod length caliper; inserting the rod and setscrews; performing segmental compression; breaking of setscrew tabs; and removing the compressor/distractor.

In some embodiments, the present surgical system includes an adaptor being employed with a surgical method including the step of inserting the implant support with a surgical site and the step of sliding a sleeve along the extender. In some embodiments, the method includes the step of securing the connector to the extenders. In some embodiments, the method includes the step of connecting a compressor/distractor with the implant support. In some embodiments, the method includes the step of actuating a rack and pinion mechanism disposed with the compressor/distractor to facilitate distraction or compression.

In some embodiments, the present surgical system includes a retractor provided to maintain the tissue in a medial-lateral orientation creating a channel for accessing the spine anatomy. An in-situ assembly allows working around the retractor when disposed with the patient. In some embodiments, the method of inserting the retractor includes: inserting a dilator between the implant supports until engagement with the bony anatomy; selecting two blades having a length in accordance with exposed markings on the one-step dilator; connecting a blade holder to manipulate the blades; manipulating the blade holders into engagement with posts of the blades; aligning a tip of the blade holder with the blade rails and closing the blade holder to obtain full retention; and sliding the blades along the dilator until engagement with the bony anatomy.

In some embodiments, the present surgical system includes a retractor connected with the blades by manipulating a retraction latch into a release position. In some embodiments, the retractor includes upper buttons that are actuated to rotate articulated arms for positioning the retractor in a default flat position. In some embodiments, the retractor is configured to engage the post of a medial blade. In some embodiments, the retractor is connected with a lateral blade. In some embodiments, the dilator can then be removed.

In some embodiments, the retractor can be fixed to the operating table. In some embodiments, the retractor blades are manipulated for angulation of the blades. In some embodiments, the retractor includes a retraction latch that is moved to an engaged position and expands the retractor to retract the tissues medial-laterally. In some embodiments, a segmental retraction can be achieved by using a retractor key.

In some embodiments, the retractor includes a medial blade that is angled to access a central part of spinal anatomy. In some embodiments, a button, such as, for example, an angulation slider of the medial arm is actuated to unlock the articulation on one arm and pushed on the other arm to lock the lateral articulation. In some embodiments, the blade holders are compressed to increase the angulation of the medial blade. The blade holders then can be removed.

In some embodiments, retraction and angulation of the blades may be adjusted by pulling the retraction latch or pressing on the upper button. In some embodiments, to resist and/or prevent damage to surrounding tissue during angulation, a shorter blade may be required medially. Blades can be disconnected in-situ during the procedure by disconnecting the blade via the end button and reconnecting a new blade. In some embodiments, the retractor can be removed such that the retractor is disconnected from the surgical table. The blade holders are re-connected to the blades to facilitate extraction from the operating field. The end buttons are actuated to disconnect the blades from the retractor.

In some embodiments, the present surgical system is employed with a surgical technique for the implantation of spinal implants, such as, for example, spinal rods and setscrews. In some embodiments, the spinal rods and setscrews are implanted percutaneously. In some embodiments, the spinal rods are reduced relative to a screw head. In some embodiments, the present surgical system is employed with a surgical technique for release of screw head mobility. In some embodiments, the present surgical system is employed with a surgical technique for release of pressure applied during spinal rod reduction.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis, kyphosis and other curvature abnormalities, tumor and fractures. In some embodiments, the present disclosure may be employed with other osteal and bone-related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternative embodiments are disclosed. Reference is made to the exemplary embodiments of the present disclosure, which are illustrated in the accompanying figures. Turning to FIGS. 1-10, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Surgical system 10 includes a surgical instrument, such as, for example, an implant support 14 and an implant support 14a, similar to implant support 14, as described herein. Implant supports 14, 14a are connectable with a spinal implant, such as, for example, a bone fastener 16. Bone fastener 16 includes a receiver 18 and a screw shaft 20, as shown in FIG. 1. Screw shaft 20 is fixed with patient tissue in use of fastener 16. Each receiver 18 is connectable with one of implant supports 14, 14a to releasably engage a surgical instrument, such as, for example, a compressor/distractor 300 to distract and/or compress tissue.

Figure 2:
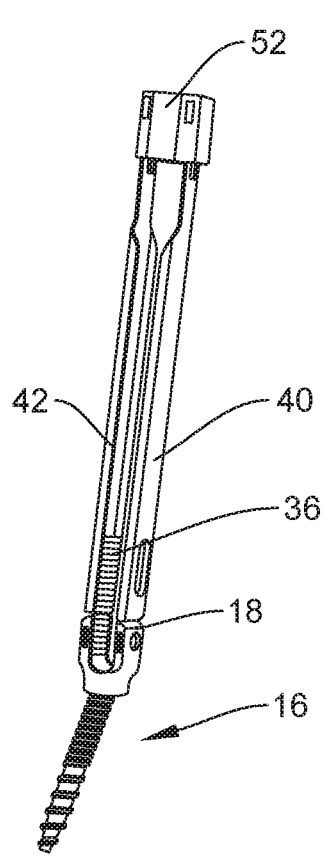
FIG. 2 is a perspective view of components of one embodiment of a surgical system in accordance with the principles of the present disclosure.
Figure 3:
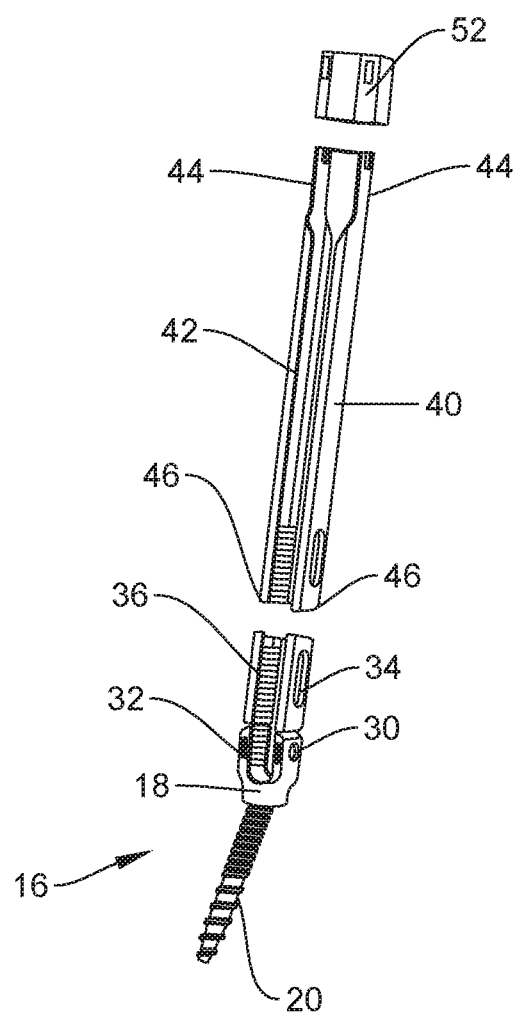
FIG. 3 is a perspective view of the components shown in FIG. 2 with parts separated.
Figure 24:
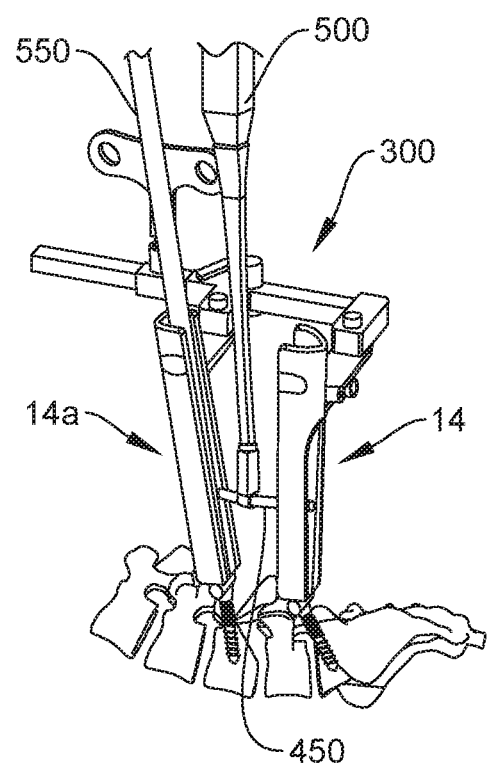
FIG. 24 is a perspective view of components of one embodiment of a surgical system disposed with vertebrae in accordance with the principles of the present disclosure.

Each receiver 18 includes a pair of spaced-apart arms 30, 32 (FIG. 3) that define an implant cavity configured for disposal of a component of a spinal construct, such as, for example, a spinal rod 450 (e.g., FIG. 24). Each receiver 18 includes an inner surface having a thread form, as shown in FIGS. 2 and 3. Bone fastener 16 includes screw shaft 20 configured to penetrate tissue, such as, for example, bone.

Arm 30 includes or is connected to a break-away tab 34 that is frangibly connected to arm 30, as shown in FIG. 2, such that manipulation of tab 34 relative to arm 30 can fracture and separate tab 34 from arm 30 at a predetermined force and/or torque limit. Arm 32 similarly includes or is connected to a break-away tab 36 that is frangibly connected to arm 32 such that manipulation of tab 36 relative to arm 32 can fracture and separate tab 36 from arm 32 at a predetermined force and/or torque limit. In some embodiments, as force and/or torque is applied to tabs 34, 36 and resistance increases, for example, the predetermined torque and force limit is approached allowing tabs 34, 36 to break off from arms 30, 32.

In some embodiments, each implant support 14, 14a includes extender tabs 40, 42 that are connectable with tabs 34, 36 and/or bone fastener 16. Each extender tab 40, 42 extends between a proximal end 44 and a distal end 46. Distal ends 46 are configured for slidable disposal of a portion of bone fastener 16, such as, for example, tabs 34, 36. In some embodiments, tabs 34, 36 are configured to releasably fix extender tabs 40, 42 to bone fastener 16 for connecting extender tabs 40, 42 to implant support 14, as described herein.

In some embodiments, an extender cap 52 is disposed with extender tabs 40, 42. Cap 60 is configured to align extenders tabs 40, 42 to resist and/or prevent splaying of extender tabs 40, 42. Cap 60 is configured as a guide to facilitate positioning of surgical instruments.

Figure 4:
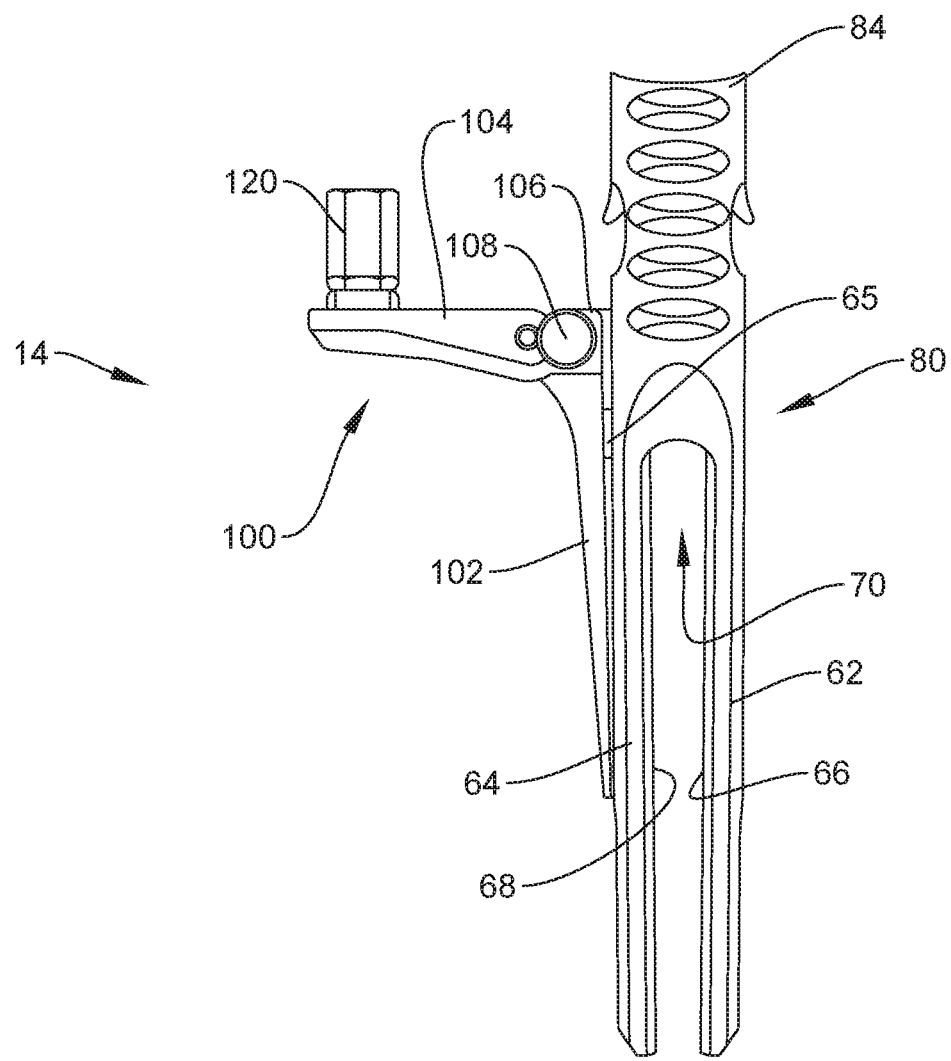
FIG. 4 is a break-away side view of components of one embodiment of a surgical system in accordance with the principles of the present disclosure.
Figure 5:
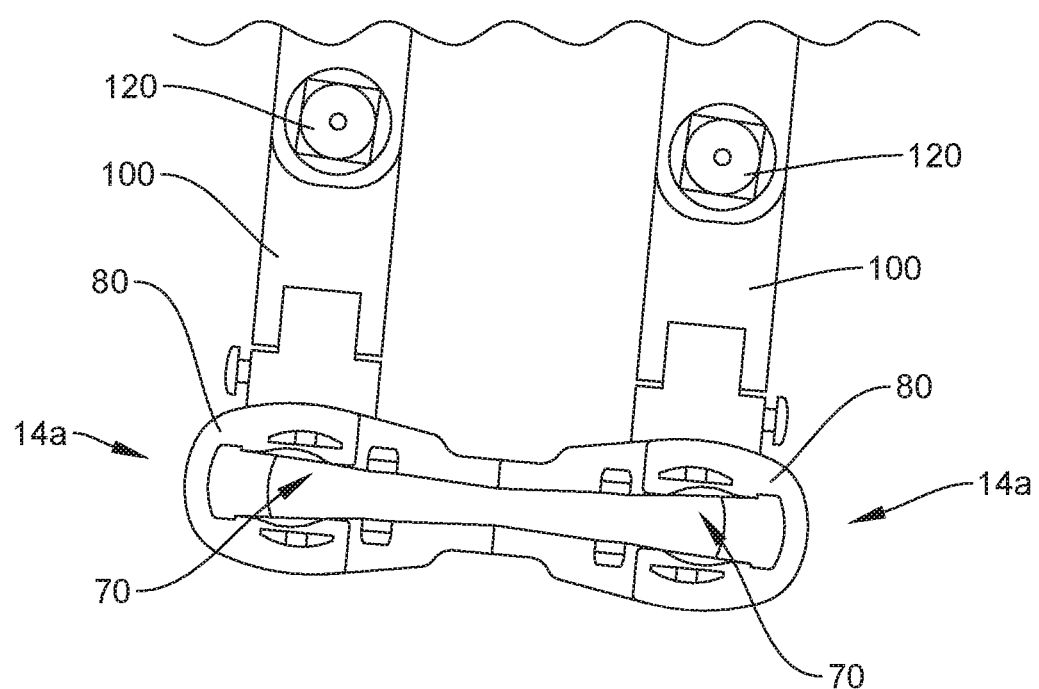
FIG. 5 is a top view of components of one embodiment of a surgical system in accordance with the principles of the present disclosure.

Implant support 14 includes a connector 80 to facilitate engagement of implant support 14 with extender tabs 40, 42. Connector 80 includes elongate members, such as, for example, sleeves 62, 64, as shown in FIGS. 4 and 5. Sleeve 62 includes a surface 66 and sleeve 64 includes a surface 68. Sleeves 62, 64 are configured for translation over extender tabs 40, 42. Sleeves 62, 64 are disposed in spaced apart relation and define a slot 70 configured for disposal of an implant, such as, for example, a spinal rod 450 (see e.g., FIG. 24).

Figure 6:
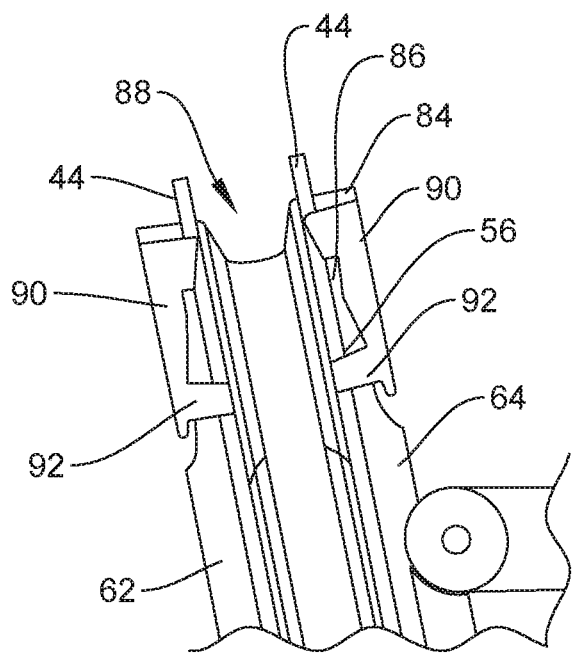
FIG. 6 is a cross section of components, taken along the line A-A in FIG. 1.

Connector 80 includes a wall 84. As shown in FIG. 6, wall 84 includes an inner surface 86 that defines a cavity, such as, for example, a pocket surface 88. Pocket surface 88 is configured for disposal of proximal ends 44 of extender tabs 40, 42, as also shown in FIG. 6. Pocket surface 88 is configured to resist and/or prevent disengagement of connector 80 from extender tabs 40, 42. In various embodiments, connector 80 includes a lock, such as, for example, a depressible button 90 configured for disposal between a lock, or locking, orientation and a non-locking orientation. In the lock orientation, button 90 releasably fixes implant support 14 with extender tabs 40, 42. In the non-locking orientation, implant support 14 is translatable relative to extender tabs 40, 42 for engagement and disengagement with bone fastener 16. Button 90 may be spring biased to a locked position, such as by a projection 92 defined by button 90 being biased in the lock orientation into engagement with a groove 56 to releasably fix implant support 14 with extender tabs 40, 42. In some embodiments, connector 80 includes one or a plurality of buttons 90.

Implant support 14 includes an adaptor 100 extending from connector 80, as shown in FIGS. 4 and 5. Adaptor 100 includes an extension 102 that extends along sleeve 64. Extension 102 is pivotally connected to sleeve 64 such that extension 102 can be rotated and/or angled, as described herein. In some embodiments, sleeve 64 includes a stopping element, such as, for example, a reinforcement rib 65 configured to resist and/or prevent rotation of extension 102 relative to sleeve 64. In some embodiments, the reinforcement element provides for an increased rigidity of implant support 14. In some embodiments, the reinforcement element resists and/or prevents inward rotation of extension 102. In some embodiments, the reinforcement element provides a reverse angle geometry to facilitate stability of extension 102.

Adaptor 100 includes an extension 104 rotatably attached with extension 102 such that extension 104 is rotatable relative to connector 80. Extension 104 extends transverse to extension 102. In some embodiments, extension 104 may be variously oriented relative to extension 102, such as, for example, perpendicular, angular and/or offset.

Extension 104 is connected with extension 102 by a pin hinge 106. Pin hinge 106 facilitates rotation of extension 104 relative to extension 102 and/or bone fastener 16. Extension 104 is rotatable through and angular range of about 0 degrees through about +/−90 degrees. In some embodiments, extension 104 includes a lock 108 configured to fix extension 104 in a selected orientation relative to extension 102 and connector 80. Lock 108 is disposable in a lock orientation and a non-locking orientation to facilitate selective orientation of extension 104. Rotation of extension 104 facilitates connection of implant support 14 to compressor/distractor 300 by providing for manipulation of implant support 14 into alignment with compressor/distractor 300, as described herein.

Figure 7:
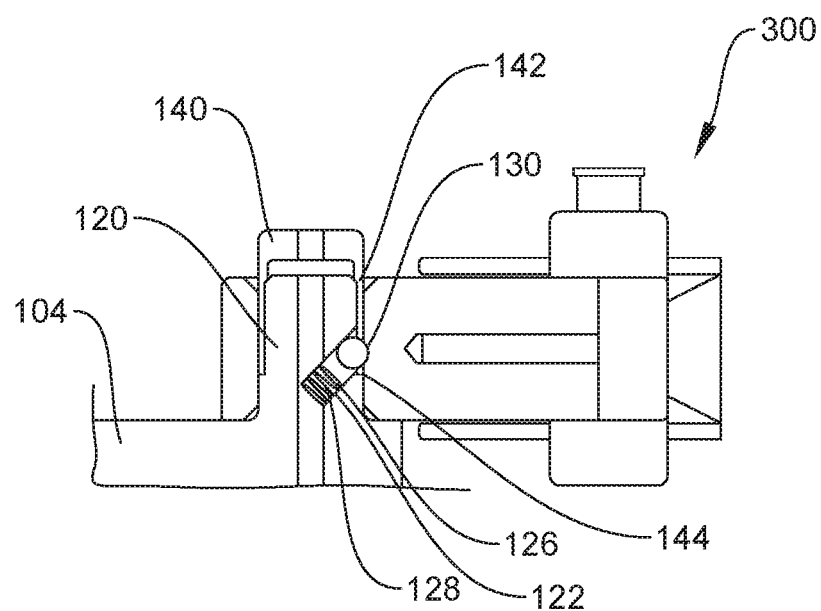
FIG. 7 is a cross section view of the components, taken along the line B-B in FIG. 1.

In various embodiments, extension 104 includes a protrusion 120 engageable with compressor/distractor 300 to releasably fix implant support 14 with compressor/distractor 300. Protrusion 120 includes a surface 122 that defines a transverse groove 126, as shown in FIG. 7. Protrusion 120 includes a lock, such as, for example, a spring-biased ball 130 that is configured for translation (and possibly also for some rotation) within groove 126 between a lock orientation and a non-locking orientation. A spring 128 disposed with groove 126 biases ball 130 toward the lock orientation.

Protrusion 120 is connectable with compressor/distractor 300. Compressor/distractor 300 includes a portion, such as, for example, a depressible button 140 configured for engagement with protrusion 120. Button 140 includes a wall 142 that extends circumferentially about protrusion 120 upon connection of compressor/distractor 300 to implant support 14. Wall 142 includes an end surface 144 that is engageable to ball 130 to translate ball 130 between the lock orientation and the non-locking orientation.

Figure 8:
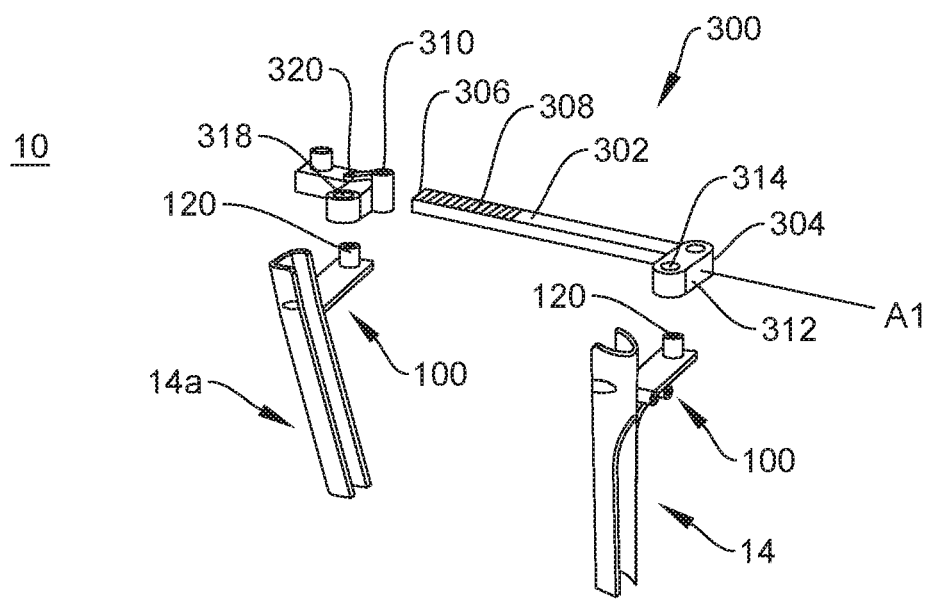
FIG. 8 is a perspective view of components of one embodiment of a surgical system in accordance with the principles of the present disclosure disposed with parts separated.

Compressor/distractor 300 includes a longitudinal element, such as, for example, a rack 302, as shown in FIG. 8. Rack 302 extends between an end 304 and an end 306 defining a longitudinal axis A1. Rack 302 is configured to connect adjacent implant supports 14, 14a to each other, as shown in FIG. 1. Rack 302 includes an outer surface having a plurality of teeth, such as, for example, splines 308 engageable with an arm 310, as described herein. Rack 302 includes an arm 312 extending from end 304. In some embodiments, arm 312 is attached with rack 302 with, for example, with clips, hooks, adhesives and/or flanges.

Arm 312 includes a surface that defines an opening 314 configured for disposal of protrusion 120 for connecting compressor/distractor 300 to implant support. Arm 310 is axially translatable along axis A1 relative to arm 312. Arm 310 includes a surface that defines an opening 318 configured for disposal of protrusion 120 for connecting compressor/distractor 300 to implant support 14a.

Compressor/distractor 300 includes a ratchet, which includes splines 308 and arm 310 engageable in a bi-directional and/or two-way ratchet configuration. Arm 310 includes a latch 320, which is engageable selectively with splines 308. In various embodiments the latch 320 includes a pinion or pawl (not shown in detail) engageable with splines 308.

Latch 320 is pivotable relative to arm 310 for disposal selectively in one or multiple positions. In various embodiments the positions include a distraction position, a neutral position, and a compression position. In the distraction position, latch 320 engages rack 302 to allow axial and/or incremental translation of arm 310 relative to arm 312/rack 302, in the direction shown by arrows B in FIG. 19. As such, distraction of vertebral tissue connected with implant supports 14, 14a can be performed. Latch 320 is pivotable relative to arm 310 for disposal in a neutral position (not shown). In the neutral position, latch 320 disengages from rack 302 to allow free axial translation of arm 310 relative to arm 312/rack 302.

Figure 9:
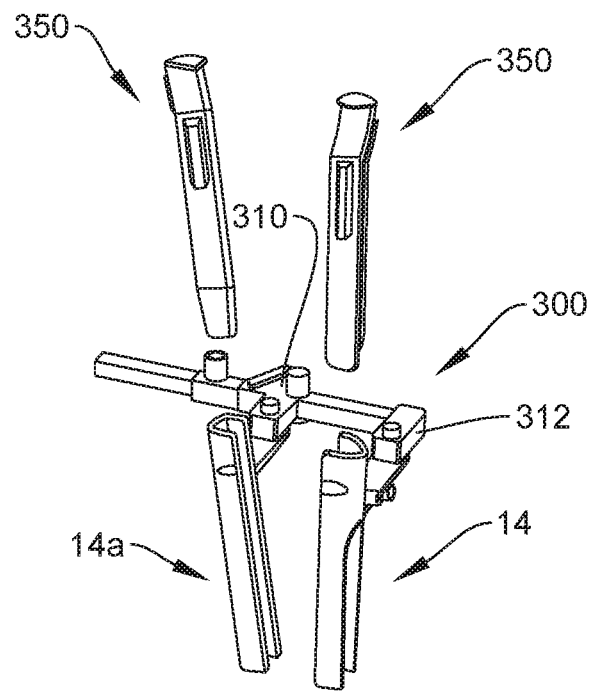
FIG. 9 is a perspective view of components of one embodiment of a surgical system in accordance with the principles of the present disclosure with some of the parts separated.
Figure 10:
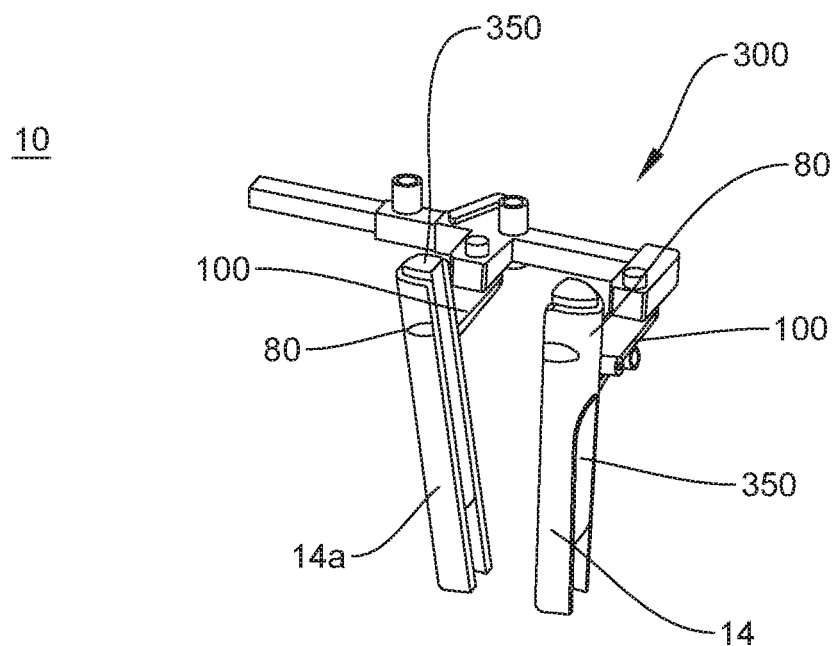
FIG. 10 is a perspective view of components of one embodiment of a surgical system in accordance with the principles of the present disclosure.

In some embodiments, surgical system 10 includes one or more alignment guides 350, as shown in FIGS. 9 and 10. Each guide 350 is configured for disposal with receiver 18 of one or more bone fasteners 16 to orient implant supports 14, 14a with respect to receiver 18 and to facilitate identifying, locating and/or engaging implant supports 14, 14a with receiver 18.

Figure 26:
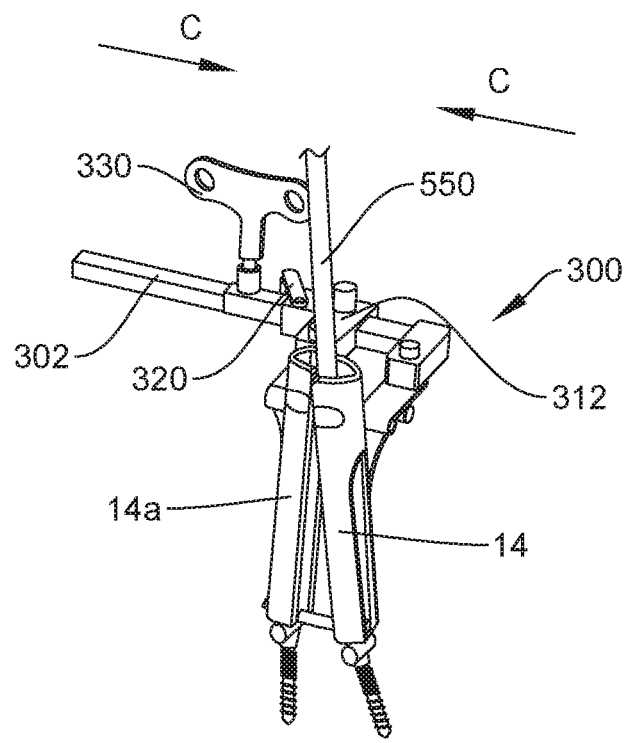
FIG. 26 is a perspective view of components of one embodiment of a surgical system disposed with vertebrae in accordance with the principles of the present disclosure.
Figure 27:
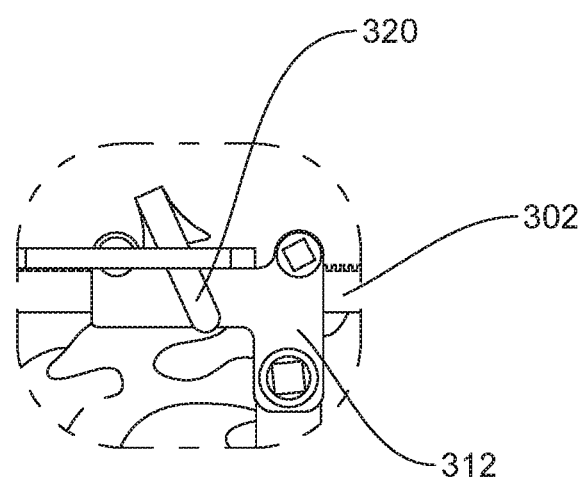
FIG. 27 is a plan view of components shown in FIG. 26.

Latch 320 is pivotable relative to arm 310 for disposal in a compression position, as shown in FIG. 26. In the compression position, latch 320 engages rack 302 to allow axial and/or incremental translation of arm 310 relative to arm 312/rack 302, in the direction shown by arrows C. As such, compression of vertebral tissue connected with implant supports 14, 14a can be performed. In some embodiments, a rotatable key 330 includes a gear surface engageable with splines 308 to axially and/or incrementally translate rack 302 to facilitate distraction and/or compression, as described herein.

In some embodiments, connection of implant supports 14, 14a to facilitate correction of a vertebral angle of vertebrae, for example, to achieve a selected lordosis and/or kyphosis, via manipulation of implant supports 14, 14a, as described herein. In some embodiments, implant supports 14, 14a are connected with compressor/distractor 300 to maintain a corrected vertebral angle of vertebrae during distraction and/or compression, as described herein.

In assembly, operation and use, surgical system 10, similar to the systems and methods described herein, is employed with a surgical procedure, for treatment of a spine of a patient including vertebrae V, as shown in FIGS. 11-30. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 12:
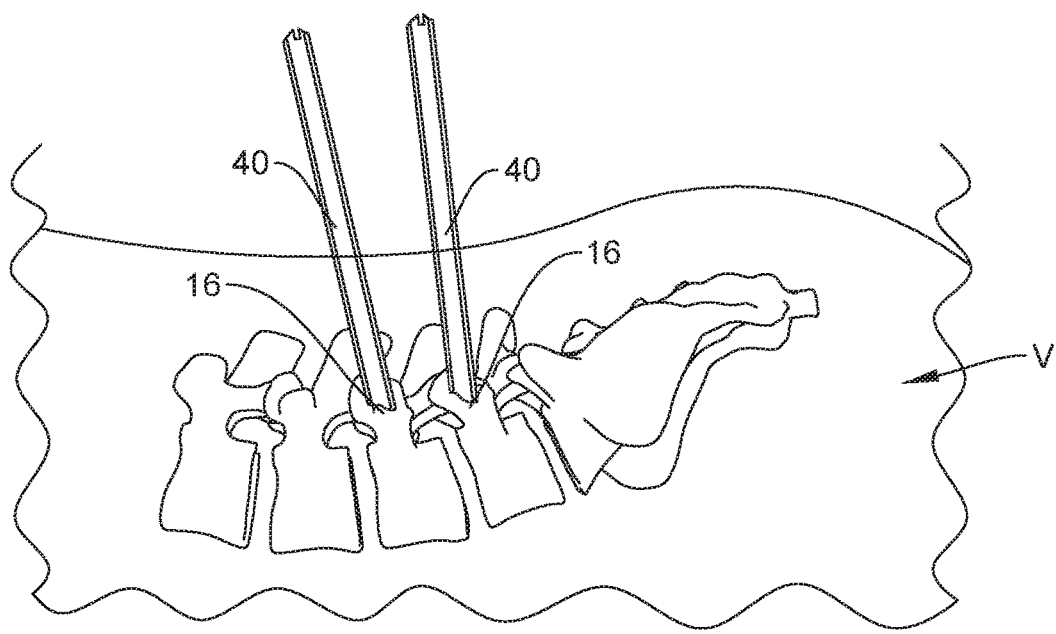
FIG. 12 is a side view of components of one embodiment of a surgical system in accordance with the principles of the present disclosure disposed with vertebrae.

Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 12. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

Figure 11:
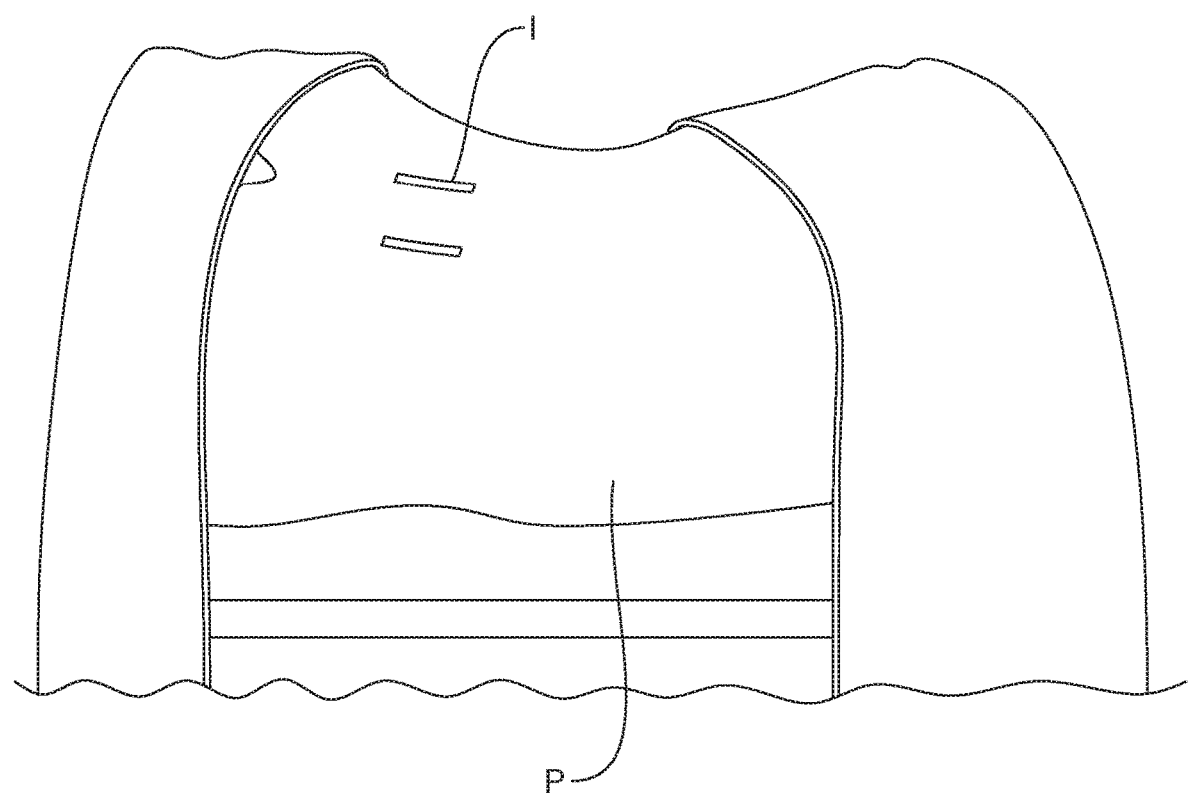
FIG. 11 is a perspective view of a patient body.

In use, to treat the affected section of vertebrae V, a medical practitioner obtains access to a surgical site including vertebrae V in any appropriate manner, such as through incision and retraction of tissues, as shown in FIG. 11. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

Figure 13:
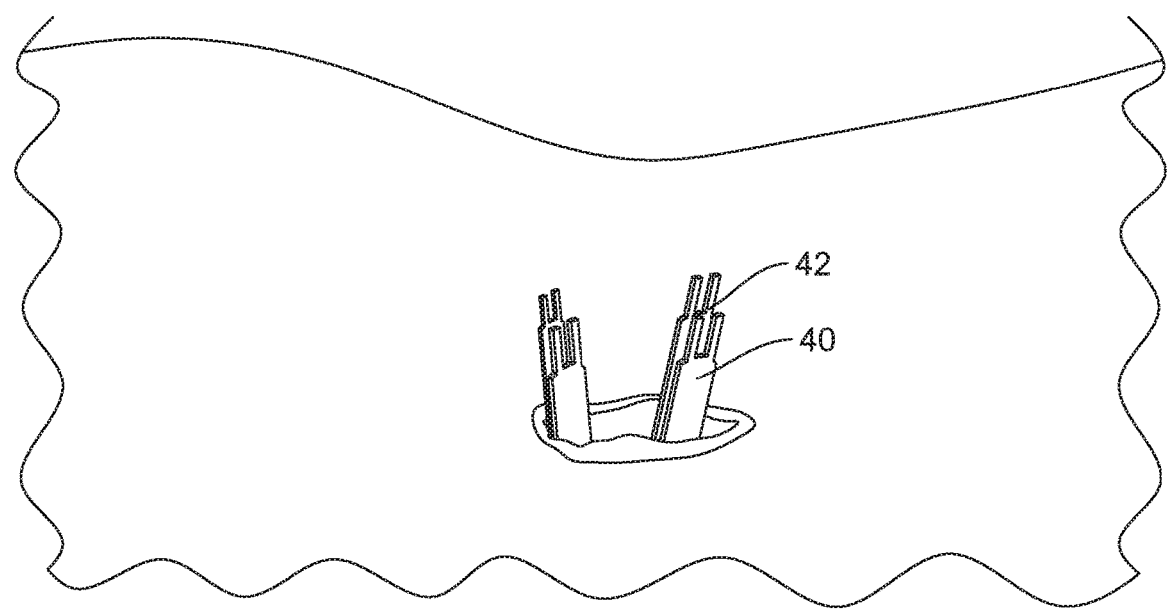
FIG. 13 is a perspective view of components of one embodiment of a surgical system in accordance with the principles of the present disclosure.
Figure 14:
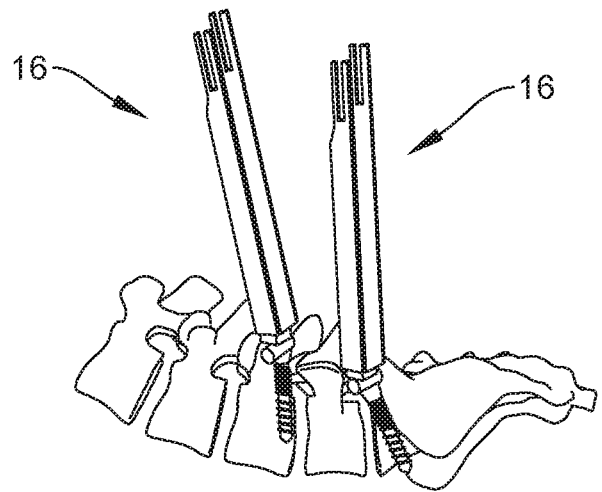
FIG. 14 is a perspective view of components of one embodiment of a surgical system disposed with vertebrae in accordance with the principles of the present disclosure.

An incision I is made in the body of a patient P and a cutting instrument (not shown) creates a surgical pathway for implantation of components of surgical system 10, as shown in FIGS. 12-14. A preparation instrument (not shown) can be employed to prepare tissue surfaces of vertebrae V, as well as for aspiration and irrigation of a surgical region.

Pilot holes or the like are made in selected vertebrae V1 and V3 for receiving bone fasteners 16. A driver (not shown) is disposed adjacent vertebrae V at a surgical site and is manipulated to drive, torque, insert or otherwise connect bone fasteners 16 with vertebrae V1 and V3. Bone fasteners 16 are engaged with vertebrae V along a lateral side L of vertebrae V, as shown in FIG. 12. Extenders 40, 42 are engaged with bone fasteners 16.

Figure 15:
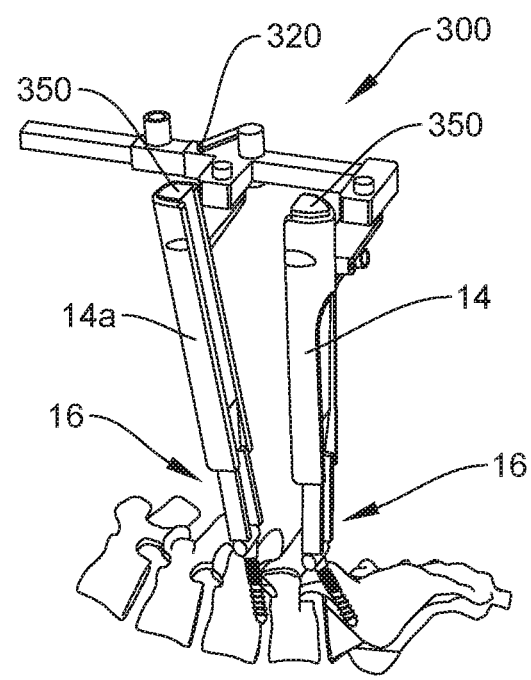
FIG. 15 is a perspective view of components of one embodiment of a surgical system disposed with vertebrae disposed with a patient body in accordance with the principles of the present disclosure.

Implant supports 14, 14*a* are connected with extenders 40, 42, as described herein. Compressor/distractor 300 is mounted with adaptors 100 via protrusion 120 for fixation therewith, as described herein. Connectors 80 capture extenders 40, 42, as shown in FIG. 15 and described herein. Compressor/distractor 300 is connected with implant supports 14, 14*a* to allow for distraction and/or compression of vertebrae V connected with extenders 40, 42.

Figure 16:
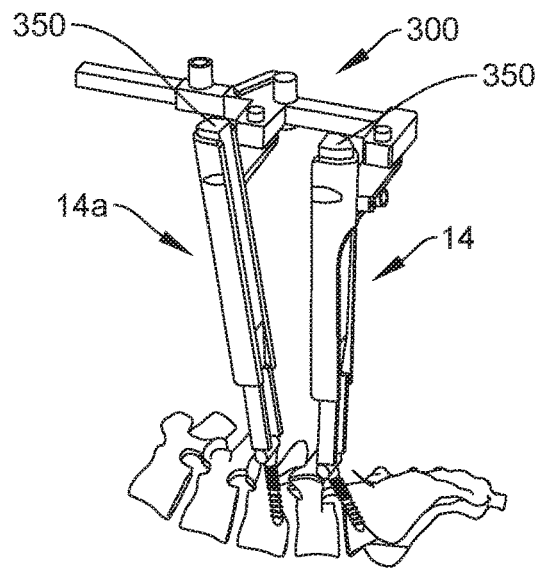
FIG. 16 is a perspective view of components of one embodiment of a surgical system disposed with vertebrae in accordance with the principles of the present disclosure.
Figure 17:
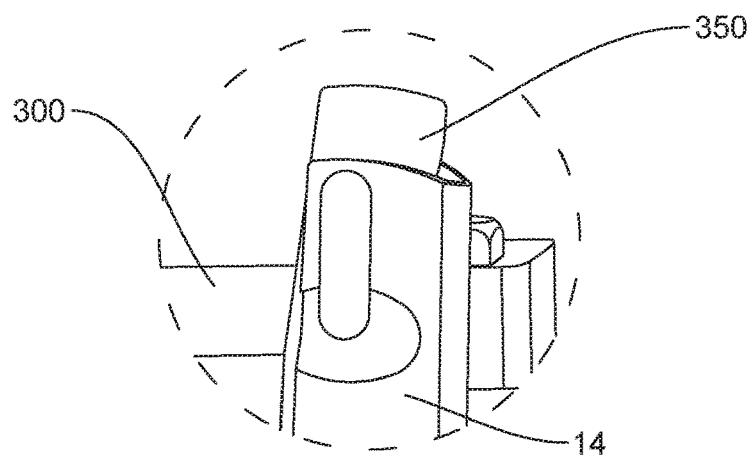
FIG. 17 is an enlarged view of detail A shown in FIG. 16.

Guide 350 is disposed with (e.g., within) connector 80. Guide 350 is translated into engagement with bone fastener 16 until fully seated with receiver 18. Guide 350 is configured to orient implant supports 14, 14*a* and facilitate identifying, locating and/or engaging implant supports 14, 14*a* with receiver 18, as shown in FIGS. 15-17.

Figure 18:
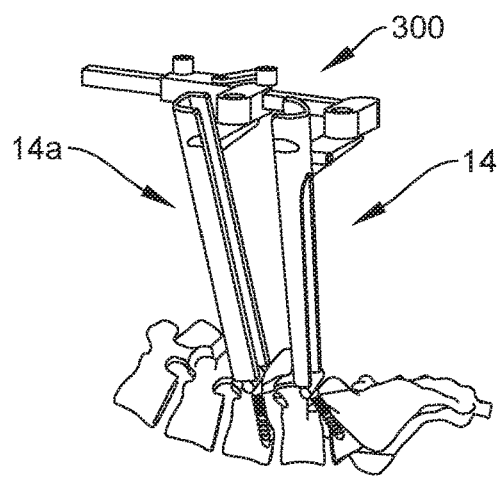
FIG. 18 is a perspective view of components of one embodiment of a surgical system disposed with vertebrae in accordance with the principles of the present disclosure.
Figure 19:
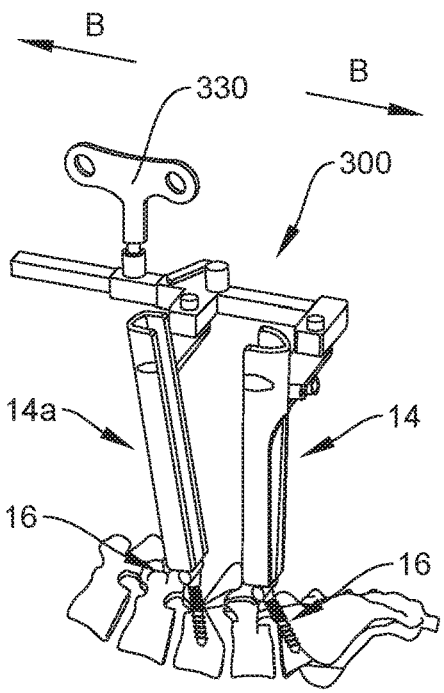
FIG. 19 is a perspective view of components of one embodiment of a surgical system disposed with vertebrae in accordance with the principles of the present disclosure.
Figure 20:
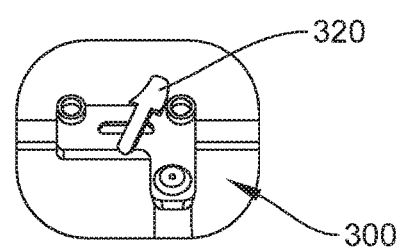
FIG. 20 is an enlarged view of detail B shown in FIG. 19.

Latch 320 is pivotable relative to arm 310 for disposal in a distraction position, as shown in FIGS. 18-20. In the distraction position, latch 320 engages rack 302 to allow axial and/or incremental translation of arm 310 relative to arm 312/rack 302, in the direction shown by arrows B in FIG. 16, to distract vertebral tissue connected with implant supports 14, 14*a*. The applied distraction forces on bone fasteners 16 will allow for opening of the foramen and the posterior wall of the spinal disc. Latch 320 can be released or re-adjusted at any time during the procedure. Latch 320 is pivotable relative to arm 310 for disposal in a neutral position (not shown). In the neutral position, latch 320 allows free axial translation of arm 310 relative to arm 312/rack 302.

Figure 21:
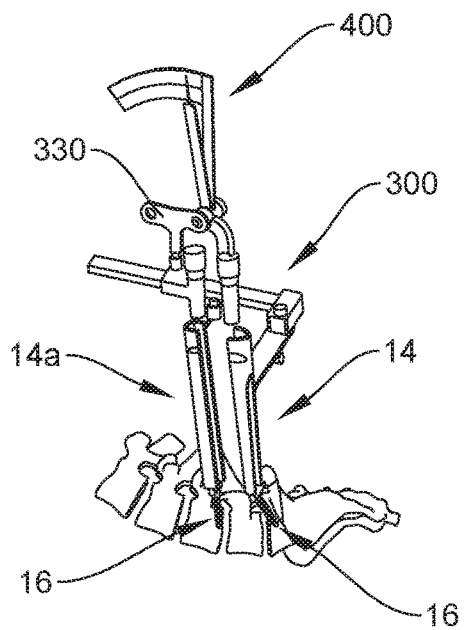
FIG. 21 is a perspective view of components of one embodiment of a surgical system disposed with vertebrae in accordance with the principles of the present disclosure.
Figure 22:
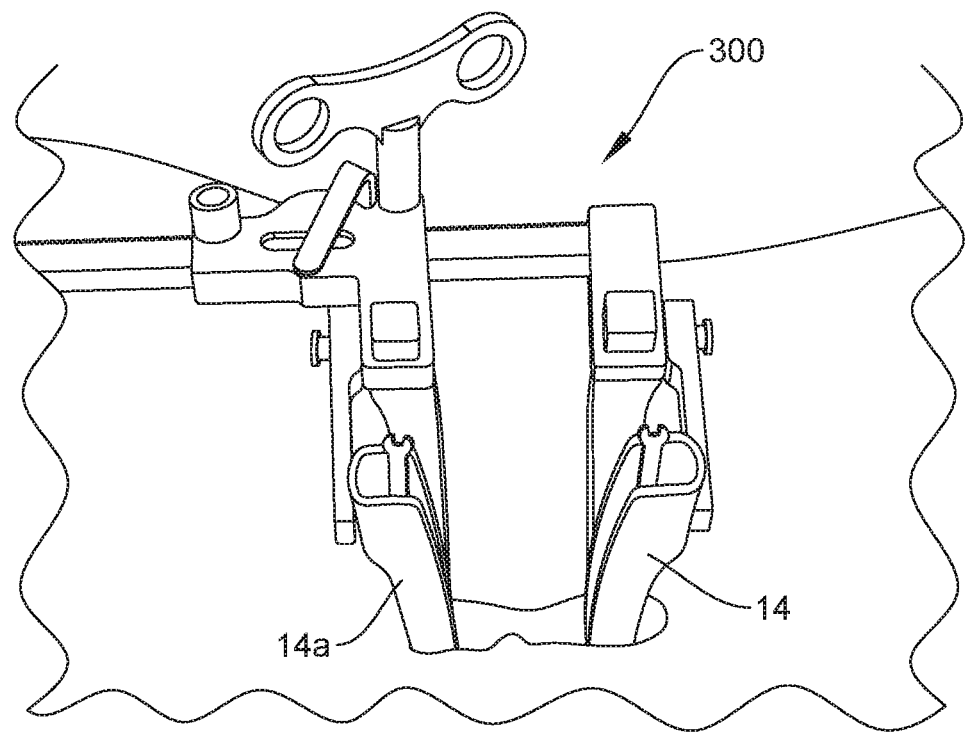
FIG. 22 is a plan view of components of one embodiment of a surgical system disposed with a patient body in accordance with the principles of the present disclosure.
Figure 23:
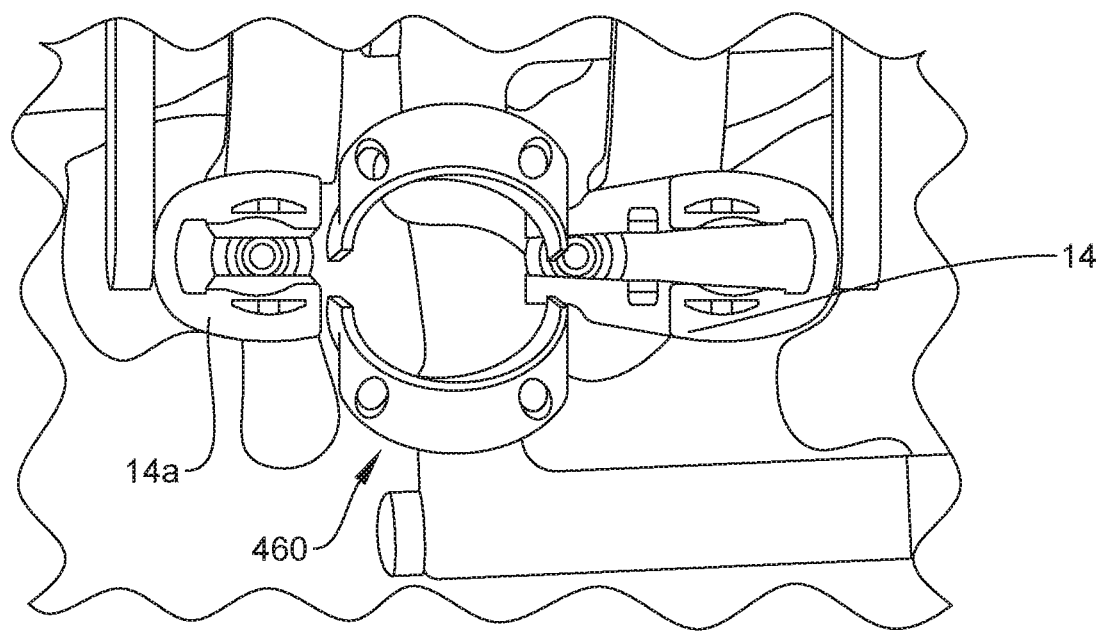
FIG. 23 is a plan view of components of one embodiment of a surgical system disposed with vertebrae in accordance with the principles of the present disclosure disposed with vertebrae.

In some embodiments, a measuring device, such as, for example, a caliper 400 is utilized to determine a length of spinal rod 450, as shown in FIG. 21. Caliper 400 is engaged with implant supports 14, 14*a* such that a distance between bone fasteners 16 can be determined. Determining the distance provides a length of rod 450 for connection with bone fasteners 16. In some embodiments, a retractor 460, as shown in FIG. 23, is disposed with tissue to form a surgical passageway to facilitate insertion of a spinal implant, such as, for example, an interbody spinal implant.

In some embodiments, a rod inserter 500 is engaged with spinal rod 450, as shown in FIG. 24. Rod inserter 500 directs and/or guides spinal rod 450 through slots 70 and into receiver 18. In some embodiments, a percutaneous endoscopic lumbar discectomy is utilized.

Figure 25:
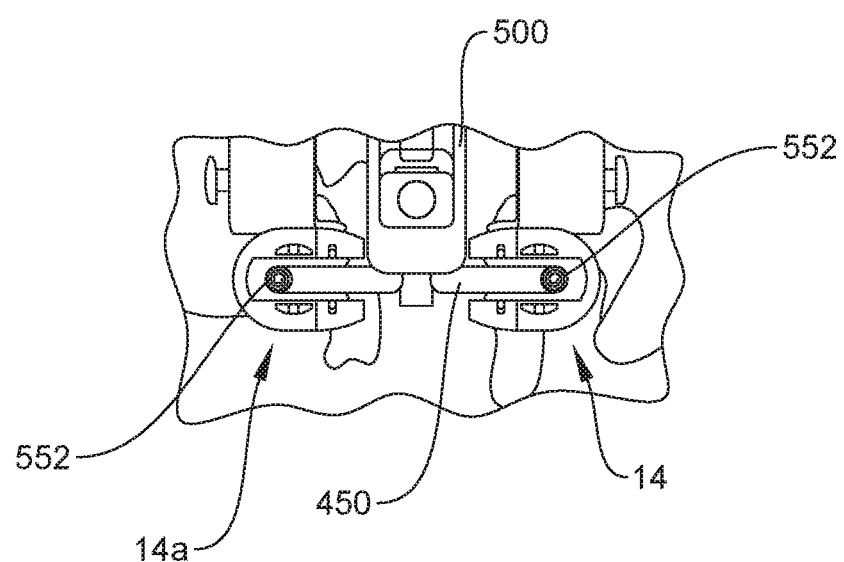
FIG. 25 a plan view of components shown in FIG. 24.

In some embodiments, a driver 550 is utilized to engage a set screw 552 with bone fasteners 16, as shown in FIGS. 24 and 25. Driver 550 directs and/or guides set screw 552 through each of implant supports 14, 14*a* into engagement with receivers 18. Set screw 552 engages receivers 18 to fix spinal rod 450. In some embodiments, if segmental compression is required, set screws 552 are loosened and latch 320 is pivotable relative to arm 310 for disposal in a compression position, as shown in FIGS. 26-28A. In the compression position, latch 320 engages rack 302 to allow axial and/or incremental translation of arm 310 relative to arm 312/rack 302, in the direction shown by arrows C, to compress vertebral tissue connected with implant supports 14, 14*a*. In some embodiments, a rotatable key 330 includes a gear surface engageable with splines 308 to axially and/or incrementally translate rack 302 to facilitate distraction and/or compression, as described herein. In some embodiments, adaptor 100 is pivotally connected to connector 80 such that connectors 80 can be rotated and/or angled, as shown in FIGS. 26-28A, to facilitate compression.

Figure 28:
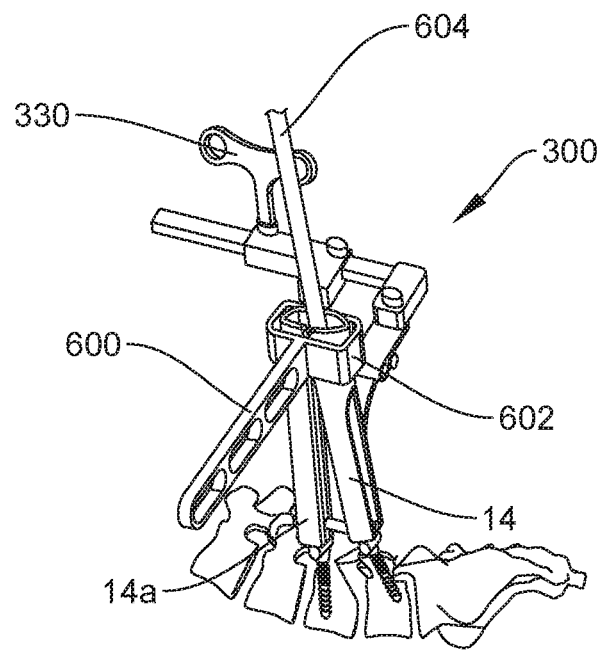
FIG. 28 is a perspective view of components of one embodiment of a surgical system disposed with vertebrae in accordance with the principles of the present disclosure.
Figure 28A:
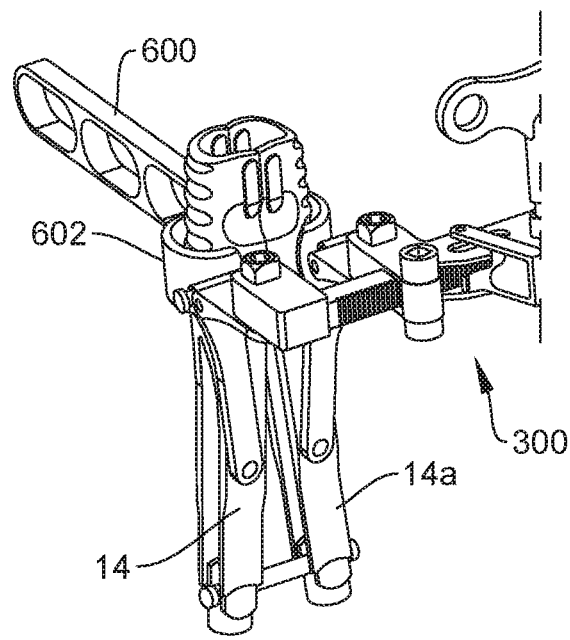
FIG. 28A is a perspective view of components of one embodiment of a surgical system in accordance with the principles of the present disclosure.
Figure 29:
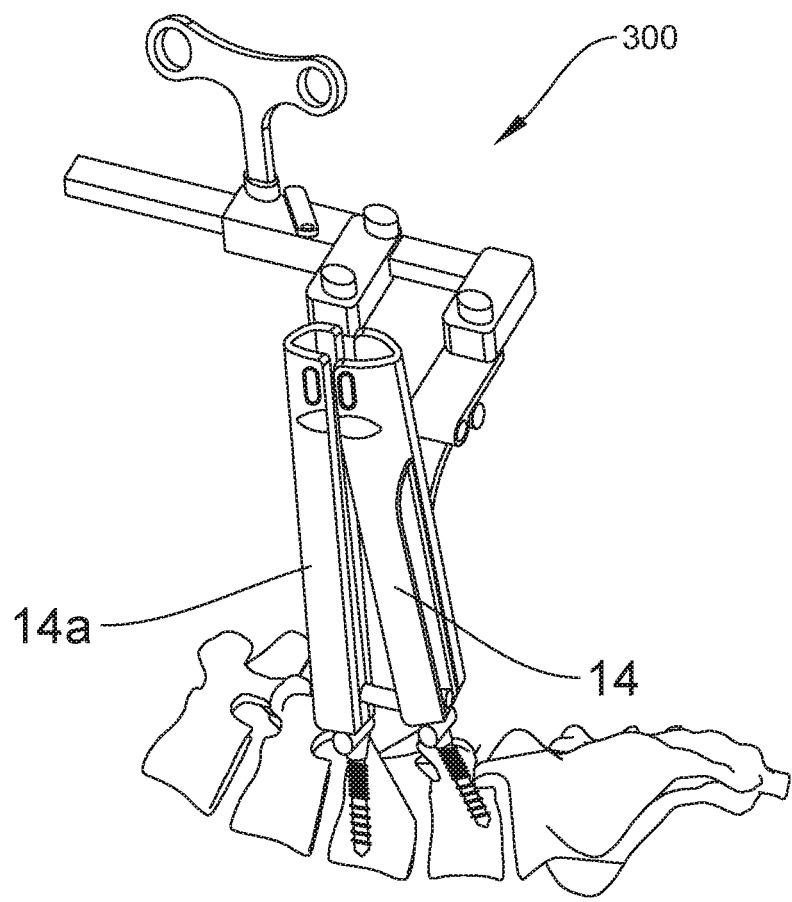
FIG. 29 is a perspective view of components of one embodiment of a surgical system disposed with vertebrae in accordance with the principles of the present disclosure.
Figure 30:
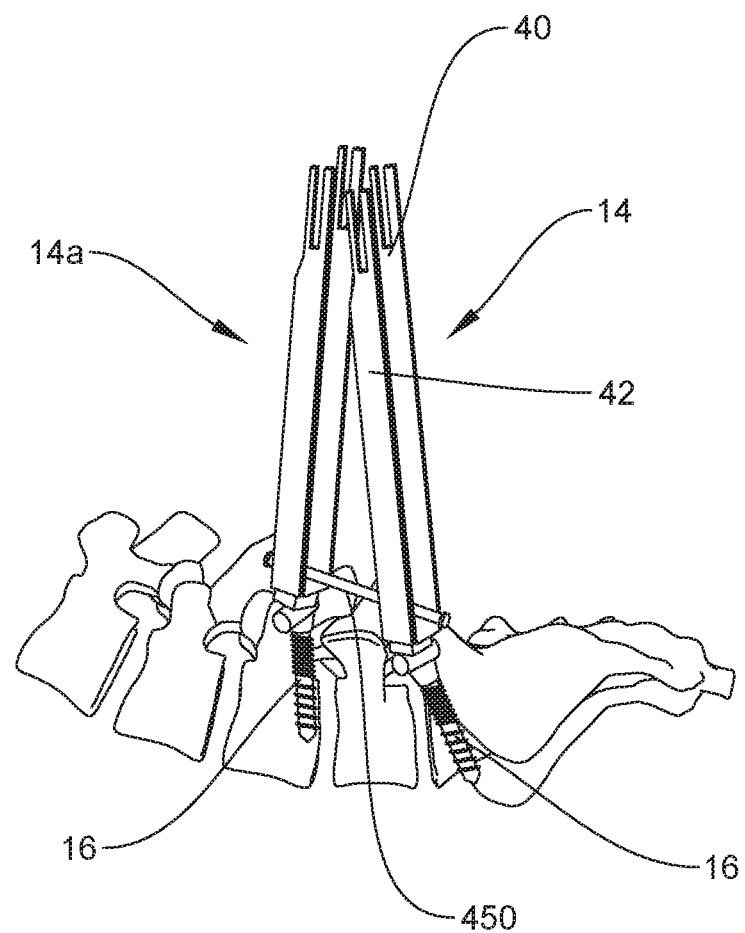
FIG. 30 is a perspective view of components of one embodiment of a surgical system disposed with vertebrae in accordance with the principles of the present disclosure.

In some embodiments, a tab hook counter torque handle 600 and a tab hook counter torque sleeve 602 are engaged with implant supports 14, 14*a*, as shown in FIGS. 28 and 28A. Handle 600 and sleeve 602 are configured to provide additional leverage to facilitate removing and/or separating a frangible or break off portion of set screw 552 at a selected torque limit. In some embodiments, counter torque sleeve 602 is configured to reinforce connection of connectors 80 and protect break-away tabs 34, 36 during break off of set screw 552. In some embodiments, connectors 80 are disposed in contact at a center of a radius of a pre-bent rod. In some embodiments, a break off handle 604 is disposed with driver 500 and is manipulated to apply a force to set screw 552 for tightening and the torque limit for break off. Compressor/distractor 300 and implant supports 14, 14*a* are removed, as shown in FIGS. 29 and 30. Vertebrae V is aligned to a selected orientation for sagittal, coronal and/or axial correction.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In one embodiment, surgical system 10 includes a retractor 800, as shown in FIGS. 31-38. The retractor 800 can in any way be like retractor 460 described herein. Retractor 800 includes a first member 802 connected to a second, mating, member 902.

Figure 31:
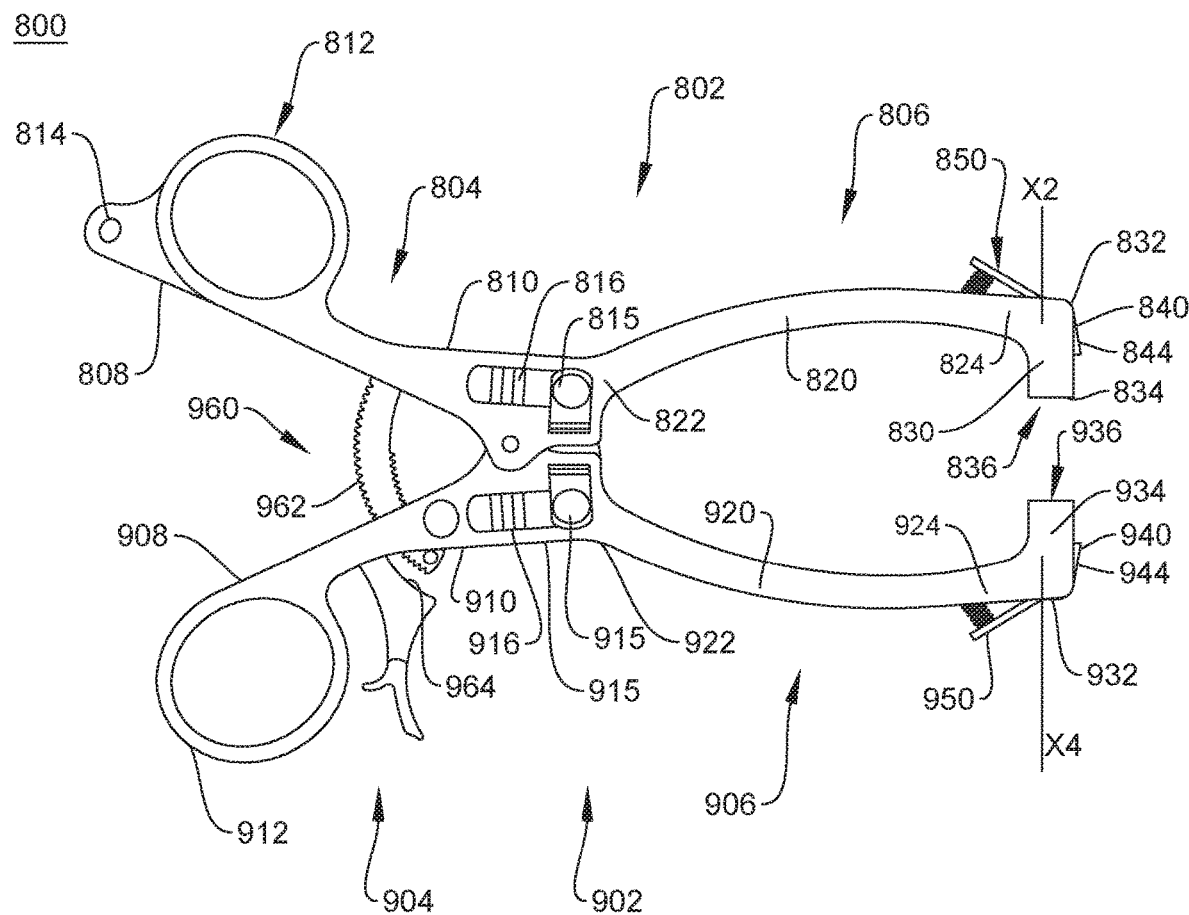
FIG. 31 is a plan view of components of one embodiment of a surgical system in accordance with the principles of the present disclosure.
Figure 32:
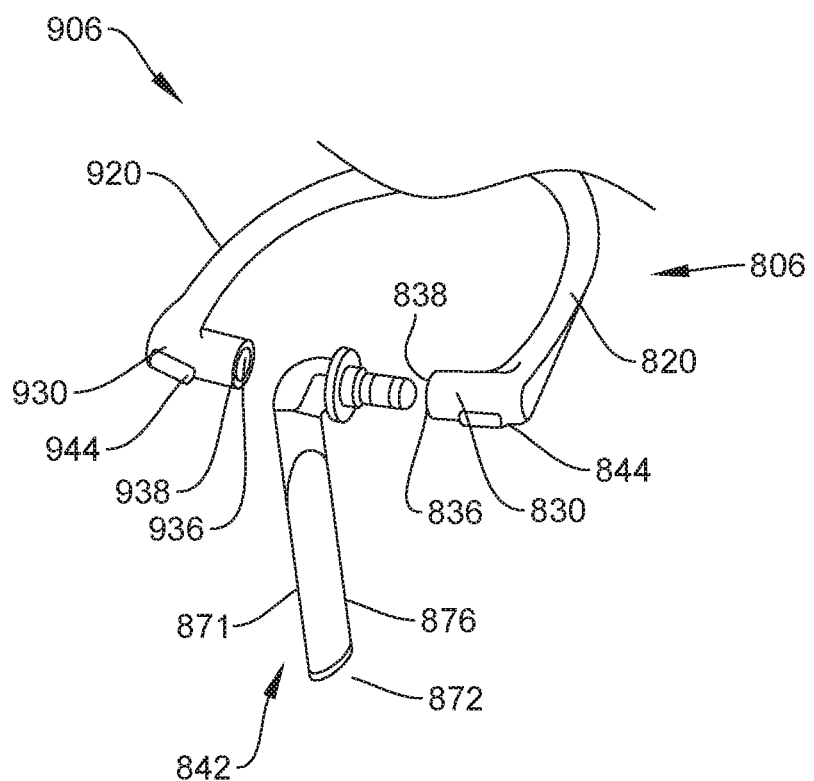
FIG. 32 is a break-away perspective view of components of one embodiment of a surgical system with parts separated.
Figure 33:
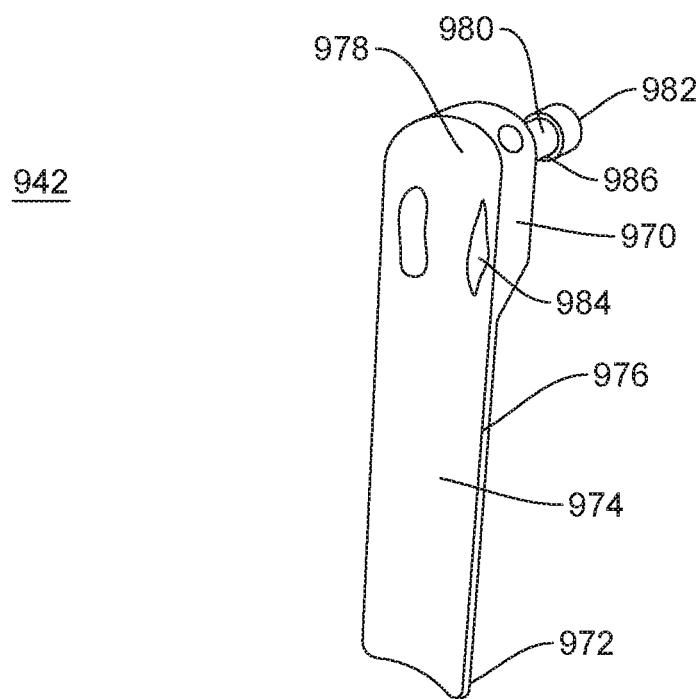
FIG. 33 is a perspective view of components of one embodiment of a surgical system in accordance with the principles of the present disclosure.
Figure 34:
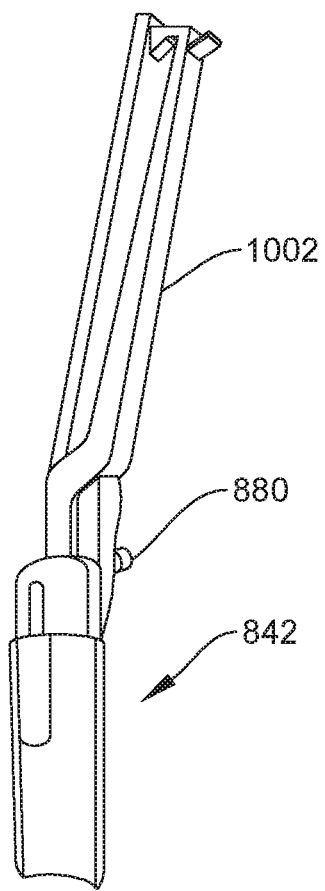
FIG. 34 is a perspective view of components of one embodiment of a surgical system in accordance with the principles of the present disclosure.

The first member 802 has a proximal portion 804 and a distal portion 806, as shown in FIG. 31. The distal portion 806 is connected or connectable to a blade 842, as shown in FIG. 32. Proximal portion 804 extends between a proximal end 808 and a distal end 810. Proximal end 808 comprises a handle 812. Distal end 810 is pivotally connected with a distal end 910 of a portion 904 of member 902, as described herein. Handle 812 includes a mating element 814 configured for engagement with a mounting device to fix retractor 800 with a surgical table (not shown).

Figure 46:
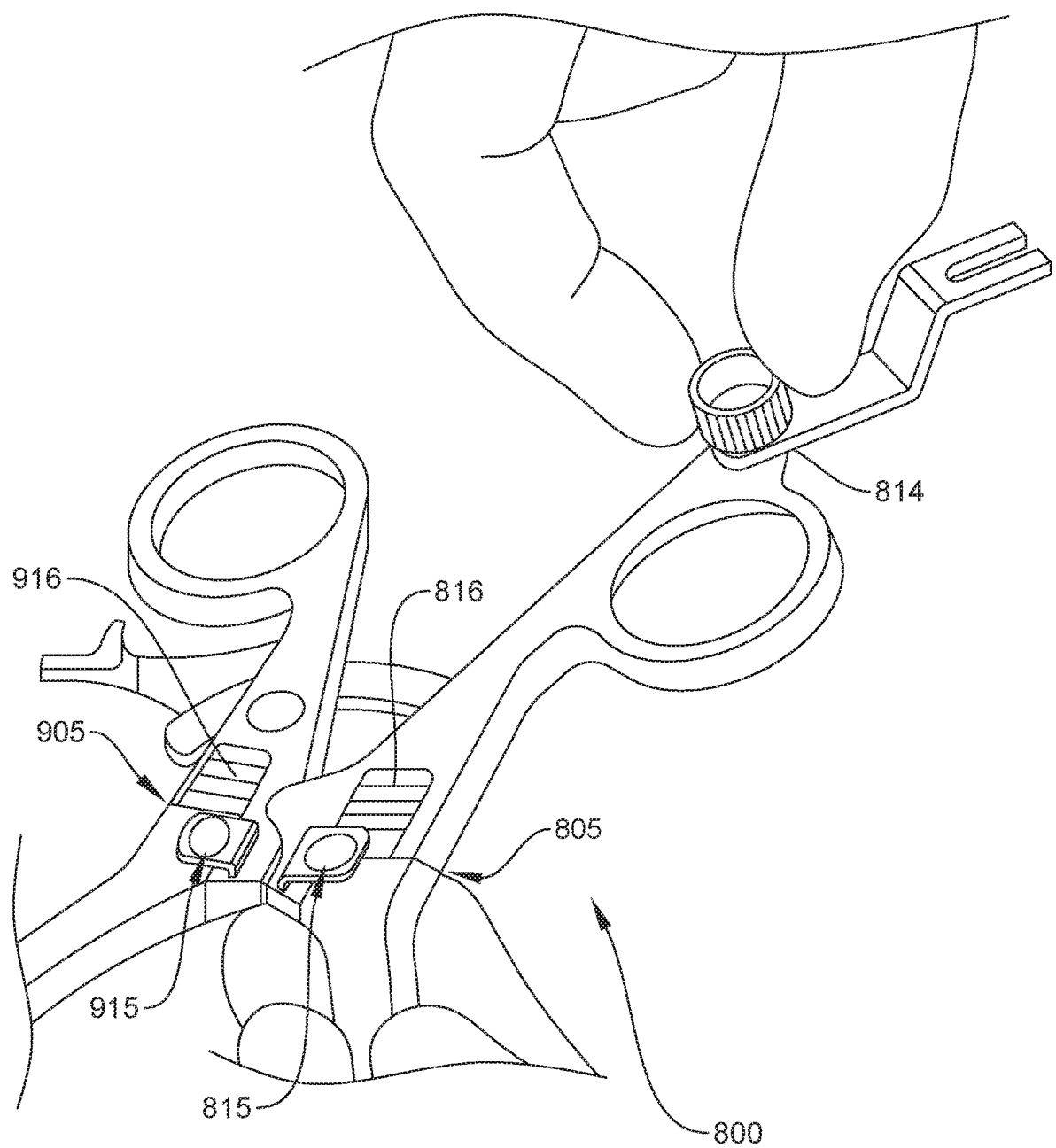
FIG. 46 is a break-away perspective view of components of one embodiment of a surgical system in accordance with the principles of the present disclosure.
Figure 47:
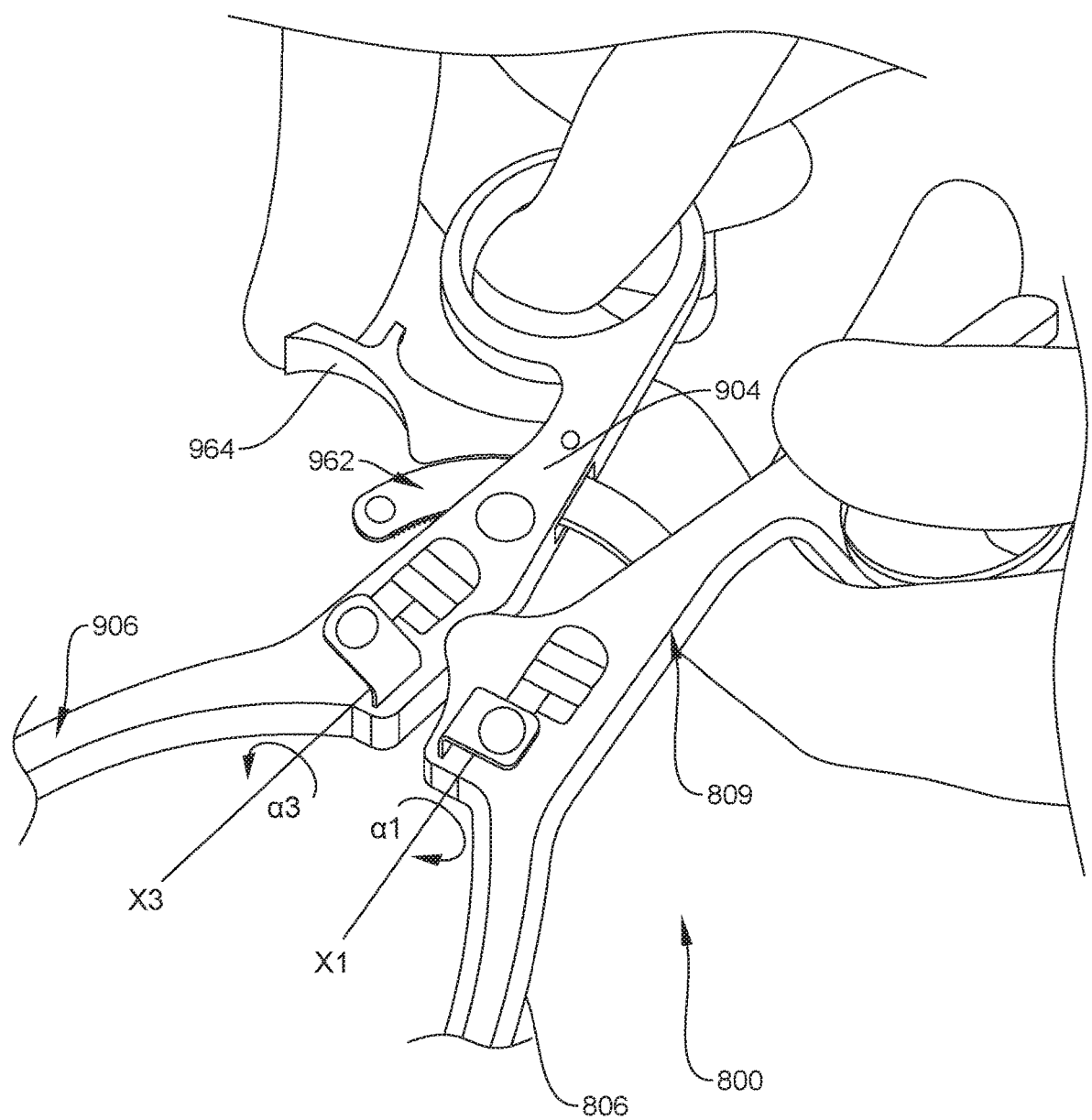
FIG. 47 is a perspective view of the components shown in FIG. 46.

Proximal portion 804 is rotationally connected with distal portion 806, such as, for example, by a pivot joint 805, as shown in FIG. 46. The pivot joint facilitates angulation of distal portion 806 and blade 842 relative to proximal portion 804. A button 815 is actuated to facilitate rotation of distal portion 806 about pivot joint 805 to a desired angulation. Button 815 controls angulation of blade 842 through an angular range α1 about an axis X1, as shown in FIG. 47. In some embodiments, angular range α1 is from about 0 degrees to about 90 degrees. In some embodiments, angular range α1 may be increased by increments of about 5 degrees between about 0 degrees to a maximum of about 90 degrees. A slider 816 is translated into engagement with button 815 to lock the desired angulation of distal portion 806 and blade 842.

Figure 36:
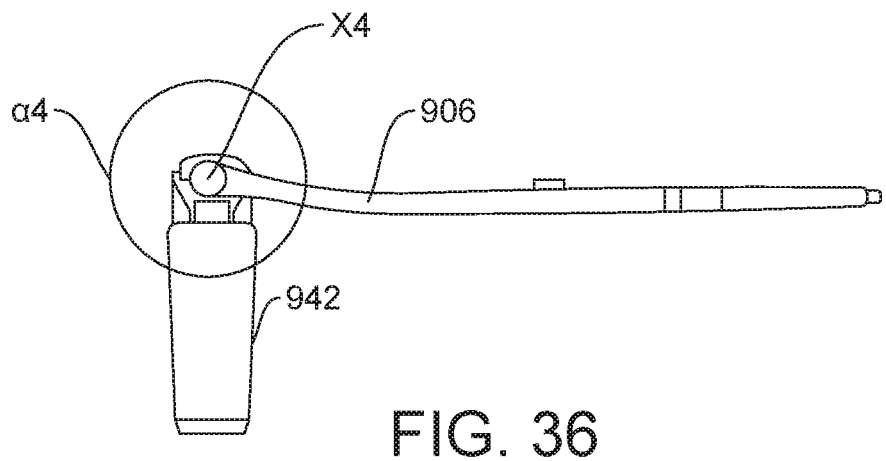
FIG. 36 is a side view of components of one embodiment of a surgical system in accordance with the principles of the present disclosure.
Figure 38:
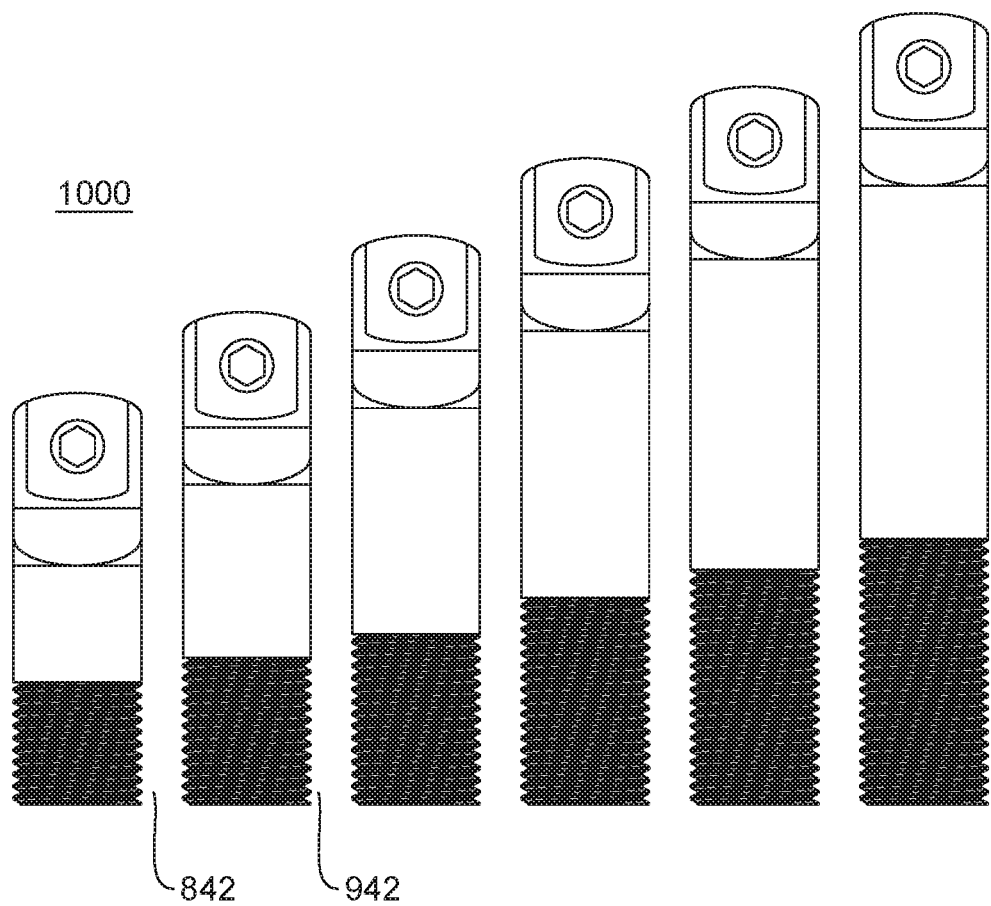
FIG. 38 is a side view of alternatively sized components of a surgical system in accordance with the principles of the present disclosure.

Distal portion 806 includes an arm 820. Arm 820 extends between a proximal end 822 and a distal end 824. In some embodiments, arm 820 may have various cross-section configurations, such as, for example, arcuate, cylindrical, oblong, rectangular, polygonal, undulating, irregular, uniform, non-uniform, consistent, variable, and/or U-shape. Distal portion 806 is configured with a profiled geometry, such as, for example, an arcuate configuration to facilitate compatibility with patient anatomy, as shown in FIGS. 36 and 38.

Figure 35:
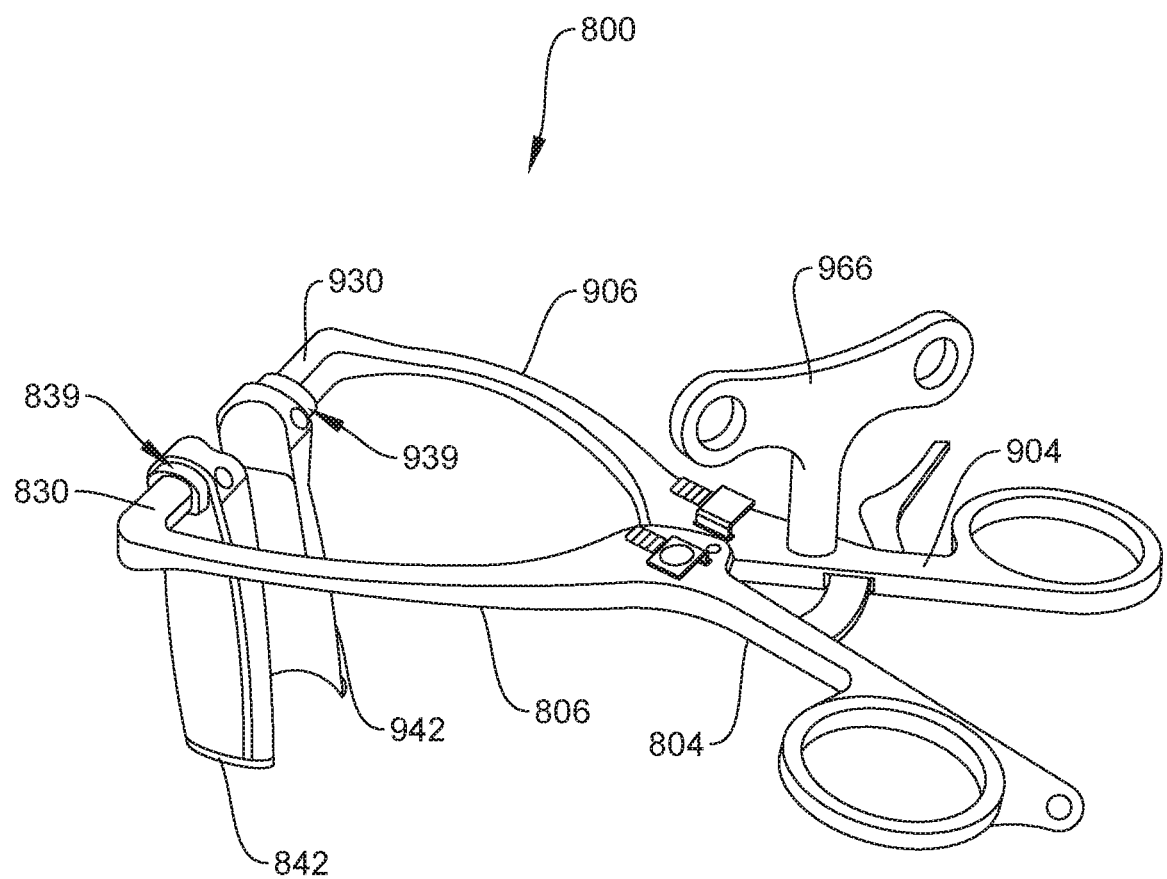
FIG. 35 is a perspective view of components of one embodiment of a surgical system in accordance with the principles of the present disclosure.
Figure 53:
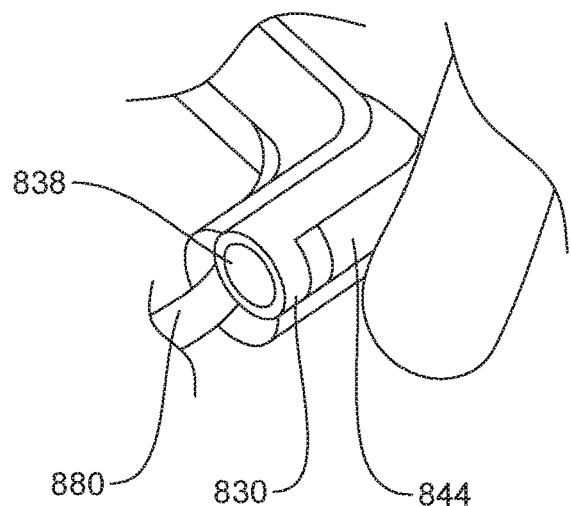
FIG. 53 is a break-away perspective view of components of one embodiment of a surgical system in accordance with the principles of the present disclosure.

Distal portion 806 includes a part 830 that extends from distal end 824. Part 830 extends between an end 832 and an end 834. Part 830 defines an axis X2. End 834 includes a surface 836, as shown in FIGS. 31 and 32, that defines a mating connection, such as, for example, a socket 838, as shown in FIG. 53. Socket 838 is configured for disposal of a portion of blade 842, or of a blade connector. Socket 838 can be configured to form a pivot joint 839, as shown in FIG. 35. Pivot joint 839 facilitates rotation of blade 842 with respect to end 830, as described herein.

Part 830 includes a lock 840 configured to releasably fix blade 842 with part 830. Lock 840 includes a depressible spring button 844 that is biased to a lock orientation. Button 844 includes a latch (not shown) disposed within socket 838 and engageable with a portion of blade 842 or a blade connector to releasably fix blade 842 with part 830. Blade 842 is releasably fixed with part 830 to facilitate changing blades 842 in situ if desired. In one embodiment, to engage a blade 842, button 844 is pressed to facilitate engagement of the blade 842 with socket 838 in a snap-fit connection, button 844 is released to fix blade 842 with part 830. To disengage, button 844 is pressed to release blade 842 from part 830.

Figure 37:
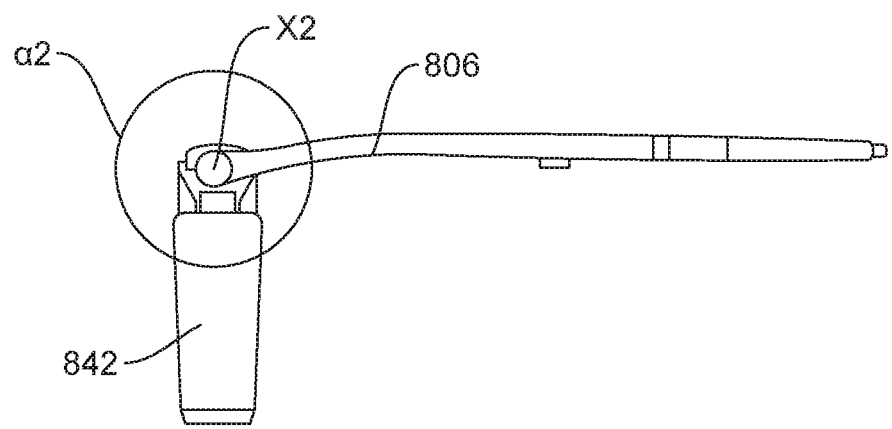
FIG. 37 is a side view of the components shown in FIG. 36.

In various embodiments, distal portion 806 includes a depressible spring button 850 that is biased to a lock orientation. Button 850 includes a latch (not shown) disposed within socket 838 and engageable with a portion of blade 842 to facilitate angulation, such as, for example, sagittal angulation, of blade 842 through an angular range α2 about axis X2, as shown in FIG. 37. For example, button 850 is pressed to release the latch to allow sagittal angulation of blade 842 via pivot joint 839. In some embodiments, the angular range α2 is about 0 degrees to about 360 degrees. In some embodiments, the angular range α2 may be changed by increments of about 10 degrees between about 0 degrees to about 360 degrees.

Second member 902 has a proximal portion 904 and a distal portion 906, as shown in FIG. 31. The distal portion 906 is connected or connectable to a blade 942, as shown in FIG. 32. Proximal portion 904 extends between a proximal end 908 and a distal end 910. Proximal end 908 comprises a handle 912. Distal end 910 is pivotally connected with a distal end 810, as described herein.

Proximal portion 904 is rotationally connected with distal portion 906, such as, for example, by a pivot joint 905, as shown in FIG. 46. The pivot joint facilitates angulation of distal portion 906 and blade 942 relative to proximal portion 904. A button 915 is actuated to facilitate rotation of distal portion 906 about pivot joint 905 to a desired angulation. Button 915 controls angulation of blade 942 through an angular range α3, as shown in FIG. 47. In some embodiments, angular range α3 is from about 0 degrees to about 90 degrees. In some embodiments, angular range α3 may be increased by increments of about 5 degrees between about 0 degrees to a maximum of about 90 degrees. A slider 916 is translated into engagement with button 915 to lock the desired angulation of distal portion 906 and blade 942.

Distal portion 906 includes an arm 920. Arm 920 extends between a proximal end 922 and a distal end 924. In some embodiments, arm 920 may have various cross-section configurations, such as, for example, arcuate, cylindrical, oblong, rectangular, polygonal, undulating, irregular, uniform, non-uniform, consistent, variable, and/or U-shape. Distal portion 906 is configured with a profiled geometry, such as, for example, an arcuate configuration to facilitate compatibility with patient anatomy, as shown in FIGS. 36 and 38.

Distal portion 906 includes a part 930 that extends from distal end 924. Part 930 extends between an end 932 and an end 934. Part 830 defines an axis X4. End 934 includes a surface 936, as shown in FIGS. 31 and 32, that defines a mating connection, such as, for example, a socket 938, as shown in FIG. 53. Socket 938 is configured for disposal of a portion of blade 942, or of a blade connector. Socket 938 can be configured to form a pivot joint 939, as shown in FIG. 35. Pivot joint 939 facilitates rotation of blade 942 with respect to end 930, as described herein.

Part 930 includes a lock 940 configured to releasably fix blade 942 with part 930. Lock 940 includes a depressible spring button 944 that is biased to a lock orientation. Button 944 includes a latch (not shown) disposed within socket 938 and engageable with a portion of blade 942 or a blade connector to releasably fix blade 942 with part 930. Blade 942 is releasably fixed with part 930 to facilitate changing blades 942 in situ if desired. In one embodiment, to engage a blade 942, button 944 is pressed to facilitate engagement of the blade 942 with socket 938 in a snap-fit connection, button 944 is released to fix blade 942 with part 930. To disengage, button 944 is pressed to release blade 942 from part 930.

In various embodiments, distal portion 906 includes a depressible spring button 950 that is biased to a lock orientation. Button 950 includes a latch (not shown) disposed within socket 938 and engageable with a portion of blade 942 to facilitate angulation, such as, for example, sagittal angulation, of blade 942 through an angular range α4 about axis X4, as shown in FIG. 37. For example, button 950 is pressed to release the latch to allow sagittal angulation of blade 942 via pivot joint 939. In some embodiments, the angular range α4 is about 0 degrees to about 360 degrees. In some embodiments, the angular range α4 may be changed by increments of about 10 degrees between about 0 degrees to about 360 degrees.

Portions 804, 806 include a ratchet 960 configured to releasably fix portions 806, 906 and to relatively fix blades 842, 942 in a selected orientation, as described herein. Ratchet 960 includes a rack 962 having plurality of teeth engageable with a latch 964 such that blades 842, 942 are selectively and/or incrementally adjustable to a selected configuration, as described herein. In some embodiments, a rotatable key 966, as shown in FIG. 35, includes a gear surface engageable with ratchet 960 to facilitate retraction, as described herein. In some embodiments, rachet 960 provides for 60 mm of tissue retraction. In some embodiments, retraction of tissue may be greater than 60 mm.

Blade 842 extends between an end 870 and an end 872. Blade 842 includes an inner surface 874 and an outer surface 876 configured for engagement with tissue. In some embodiments, all or only a portion of blade 842 may have various cross-section configurations, such as, for example, arcuate, cylindrical, oblong, rectangular, polygonal, undulating, irregular, uniform, non-uniform, consistent, variable, and/or U-shape. In some embodiments, blade 842 comprises titanium to facilitate a reduced radio-opacity. In some embodiments, blade 842 can be made from carbon fiber, aluminum and or PEEK. In some embodiments, surface 876 includes a roughened surface, for example, retention teeth configured to stabilize blade with tissue.

Blade 842 includes a head 878 disposed at end 870. Head 878 includes a post 880 extending therefrom. Post 880 includes a pivot surface 882 engageable with socket 838 to facilitate rotation of blade 842, as described herein. In some embodiments, head 878 includes a surface 884 that defines one or a plurality of passageways 886. Passageways 886 are configured for disposal of a light source (see e.g., FIG. 55).

Blade 942 extends between an end 970 and an end 972. Blade 942 includes an inner surface 974 and an outer surface 976 configured for engagement with tissue. In some embodiments, all or only a portion of blade 942 may have various cross-section configurations, such as, for example, arcuate, cylindrical, oblong, rectangular, polygonal, undulating, irregular, uniform, non-uniform, consistent, variable, and/or U-shape. In some embodiments, blade 942 comprises titanium to facilitate a reduced radio-opacity. In some embodiments, blade 842 can be made from carbon fiber, aluminum and or PEEK. In some embodiments, surface 976 includes a roughened surface, for example, retention teeth configured to stabilize blade with tissue.

Blade 942 includes a head 978 disposed at end 970. Body 978 includes a post 980 extending therefrom. Post 980 includes a pivot surface 982 engageable with socket 938 to facilitate rotation of blade 942, as described herein. In some embodiments, head 978 includes a surface 984 that defines one or a plurality of passageways 986. Passageways 986 are configured for disposal of a light source, for example, fiberoptic light cables (see e.g., FIG. 55).

In some embodiments, surgical system 10 comprises a kit 1000 of blades 842, 942, such as that shown in FIG. 38. In some embodiments, blades 842, 942 are selected from a kit of a plurality of blades 842, 942 for selective interchangeable connection with retractor 800. In some embodiments, the kit of blades 842, 942 includes alternatively configured blades 842, 942 having varied configurations, such as, for example, lengths, widths and/or shapes needed for various procedures and/or patient anatomy. In some embodiments, blades 842, 942 may have a length in a range of about 40 mm to about 90 mm. In some embodiments, blades 842, 942 are shaped such that the blades form a substantially oval cavity.

In assembly, operation and use, surgical system 10 is employed with a surgical procedure, for treatment of a spine of a patient including vertebrae V, as shown in FIGS. 11-30 and 39. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

In use, to treat the affected section of vertebrae V, a medical practitioner obtains access to a surgical site including vertebrae V in any appropriate manner, such as through incision and retraction of tissues, as described herein. An incision I is made in the body of a patient P, as described herein. Pilot holes or the like are made in selected vertebrae V1 and V3 for receiving bone fasteners 16, as described herein. Implant supports 14, 14a are connected with extenders 40, 42, as described herein. Compressor/distractor 300 is mounted with adaptors 100 via protrusion 120 for fixation therewith, as described herein. Guide 350 is disposed with connector 80, as described herein.

Latch 320 is pivotable relative to arm 310 for disposal in a distraction position, as described herein. In some embodiments, a measuring device, such as, for example, a caliper 400 is utilized to determine a length of spinal rod 450, as described herein. Caliper 400 is engaged with implant supports 14, 14a such that a distance between bone fasteners 16 can be determined, as described herein.

In some embodiments, retractor 800 is disposed with tissue to form a surgical passageway to facilitate insertion of a spinal implant, such as, for example, an interbody spinal implant.

Figures 39, 40, 41, 42:
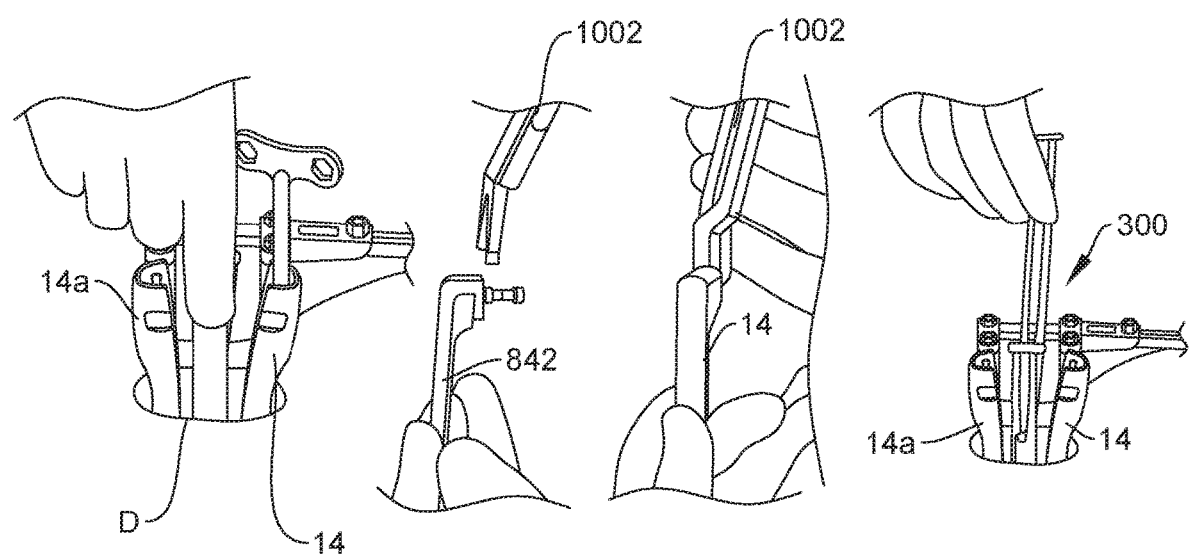
FIG. 39 is a perspective view of components of one embodiment of a surgical system disposed with a patient body.
FIG. 40 is a perspective view of components of one embodiment of a surgical system in accordance with the principles of the present disclosure.
FIG. 41 is a perspective view of components of one embodiment of a surgical system in accordance with the principles of the present disclosure.
FIG. 42 is a perspective view of components of one embodiment of a surgical system disposed with a patient body.

A dilator D is inserted between implant supports 14, 14a, as shown in FIG. 39. Dilator D is inserted to contact with bony anatomy. Blades 842, 942 are selected from kit 1000. A blade holder 1002 is attached with blade 842, as shown in FIGS. 34 and 40-42. Blade holder 1002 is utilized to manipulate blade 842. Handles of blade holder 1002 are oriented towards post 880 to align a tip of blade holder 1002 with blade rails and close blade holder to obtain full retention. Blade 842 is translated along dilator D into engagement with the bony anatomy, as shown in FIG. 42.

Figure 43:
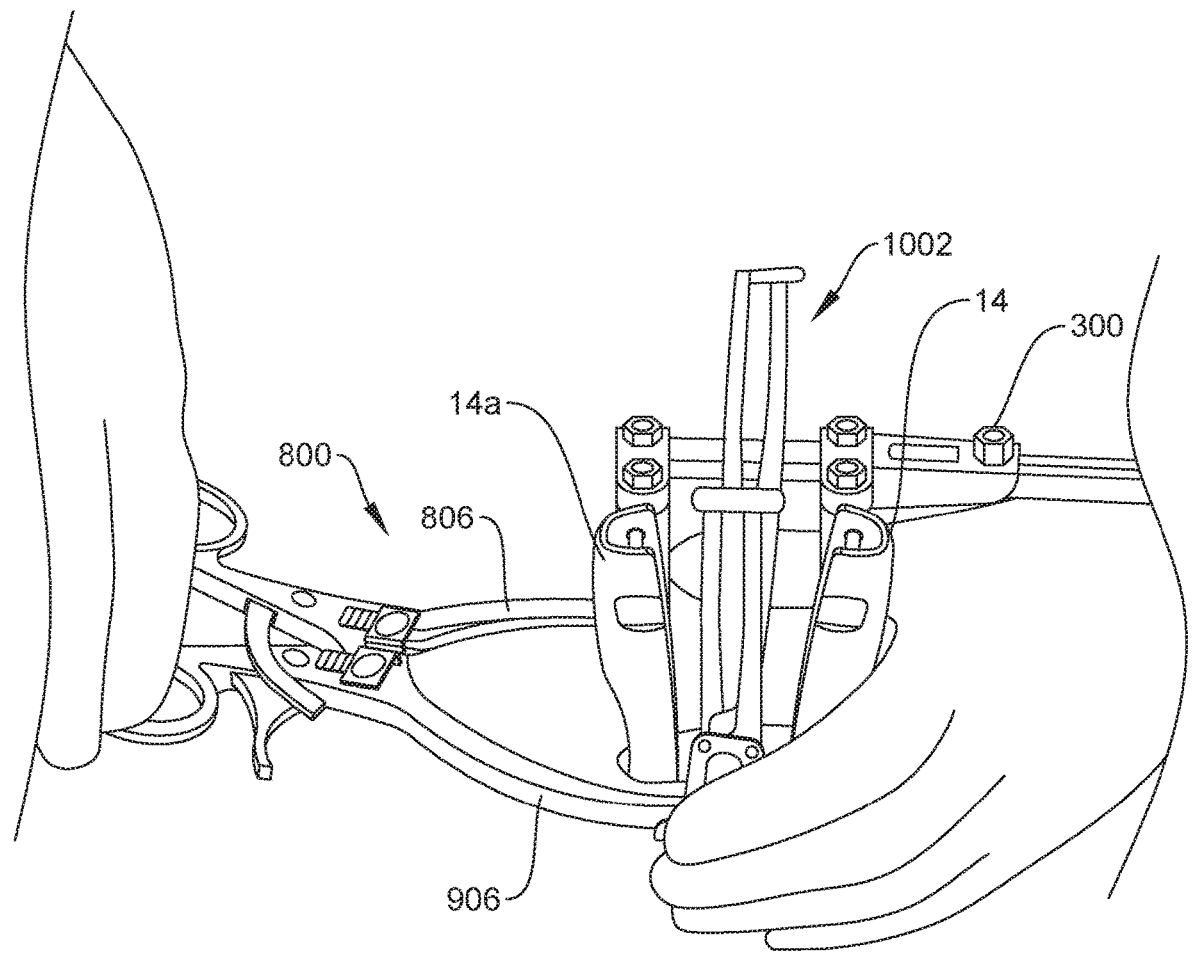
FIG. 43 is a perspective view of components of one embodiment of a surgical system disposed with a patient body.
Figure 44:
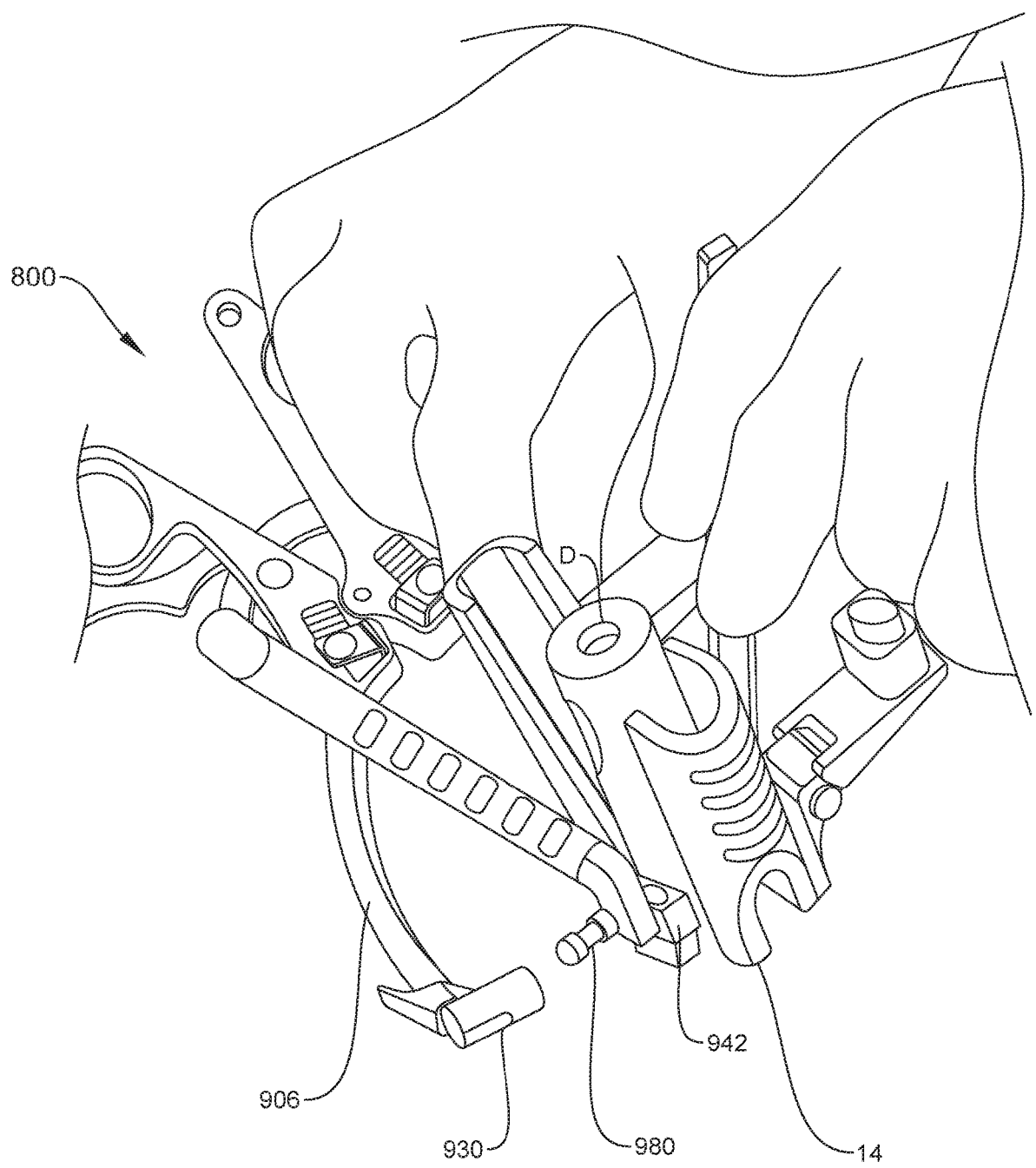
FIG. 44 is a perspective view of components of one embodiment of a surgical system disposed with a patient body.
Figure 45:
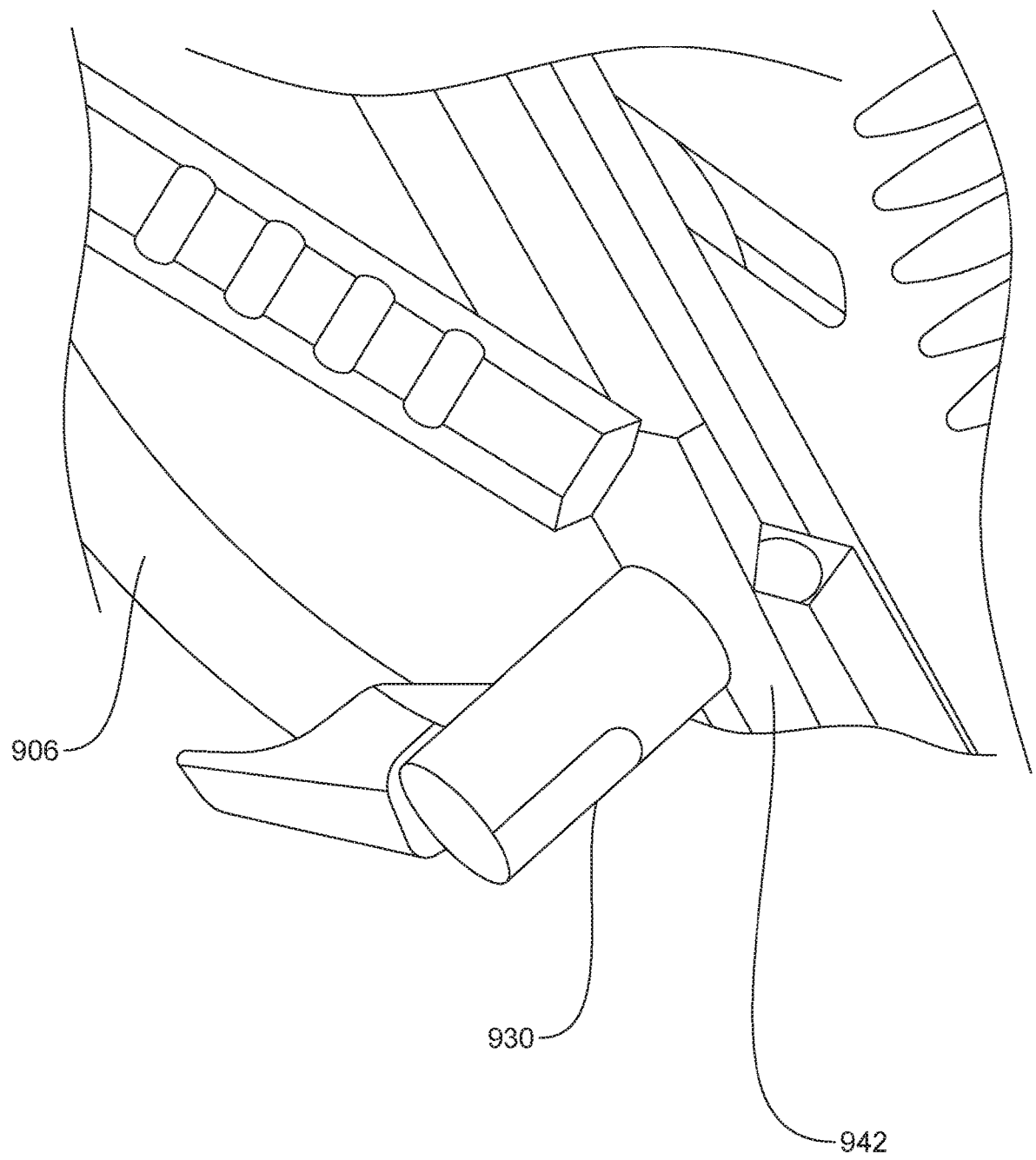
FIG. 45 is a perspective view of components of one embodiment of a surgical system disposed with a patient body.

Sliders 816, 916 are actuated to articulate portions 806, 906 to position portions 806, 906 in a default flat orientation. Handles 812, 912 are manipulated for positioning retractor 800 around implant supports 14, 14a, as shown in FIGS. 43-45. Part 830 is engaged with post 880 of blade 842. Blade 942 is inserted similar to blade 842. Portion 906 is manipulated to engage part 930 with post 980. Dilator D is removed. Retractor 800 can be connected with the surgical table via mating element 814, as shown in FIG. 46, to resist and/or prevent movement of retractor 800.

In some embodiments, pivot joints 839, 939 allow for retractor 800 to be rotated. For example, retractor 800 is disposed adjacent implant support 14a, and pivot joints 839, 939 allow retractor 800 to be rotated to the opposite side of surgical system 10, as shown by arrow M in FIG. 48, for positioning adjacent implant support 14. In some embodiments, rotation of retractor 800 facilitates viewing and/or selective positioning of retractor 800 relative to one or more components of system 10 and/or tissue.

Figure 48:
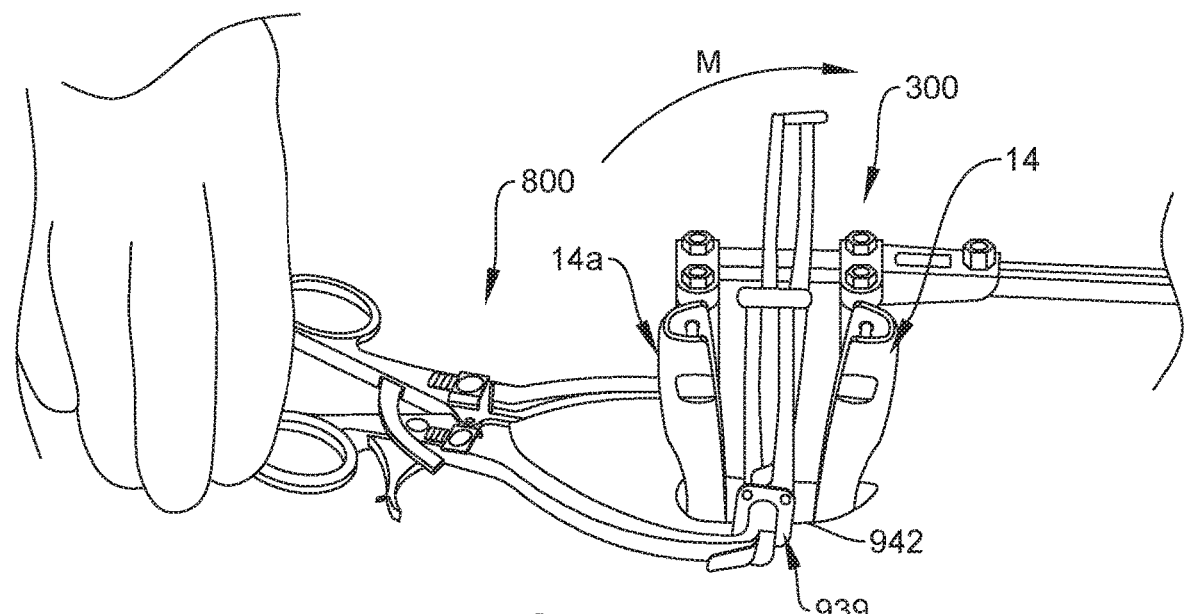
FIG. 48 is a perspective view of components of one embodiment of a surgical system disposed with a patient body.
Figure 49:
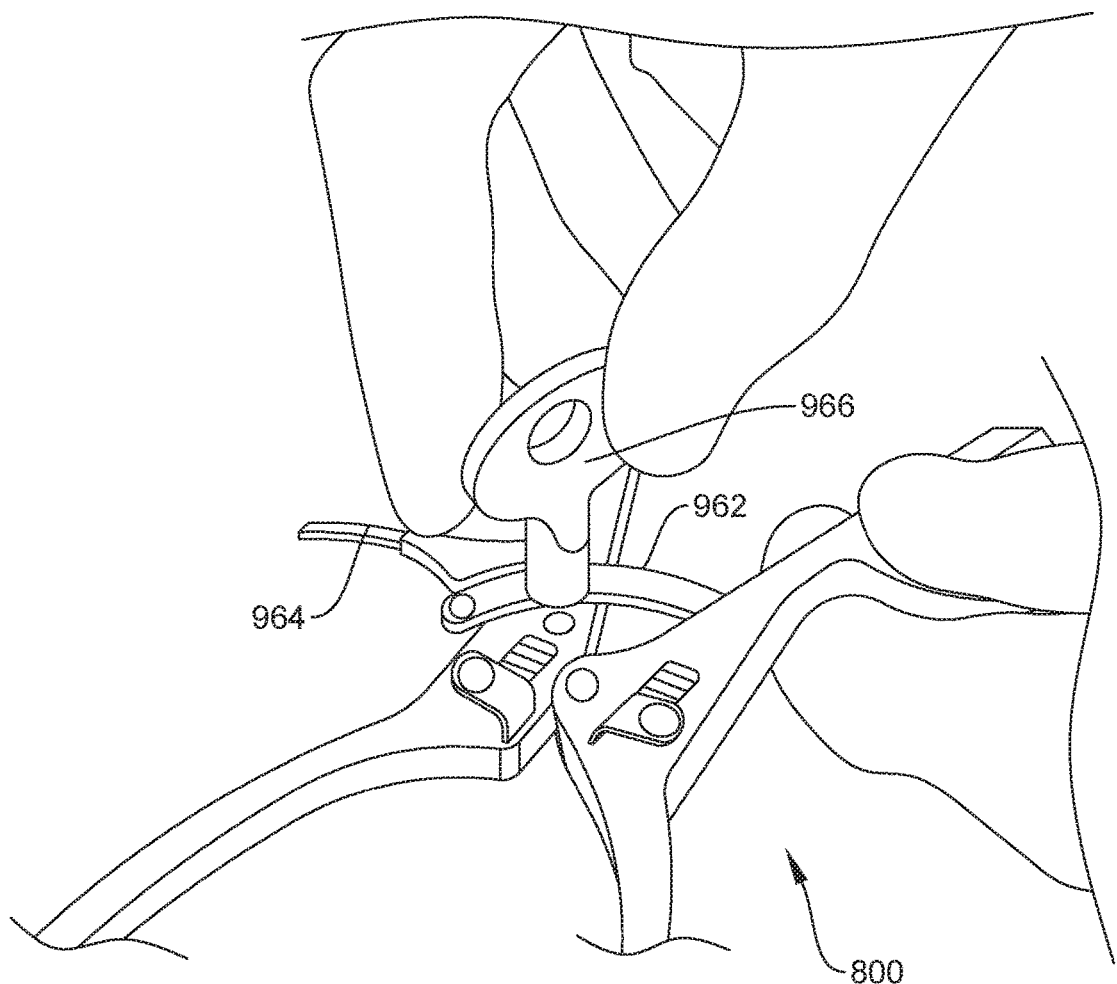
FIG. 49 is a break-away perspective view of components of one embodiment of a surgical system in accordance with the principles of the present disclosure.
Figure 50:
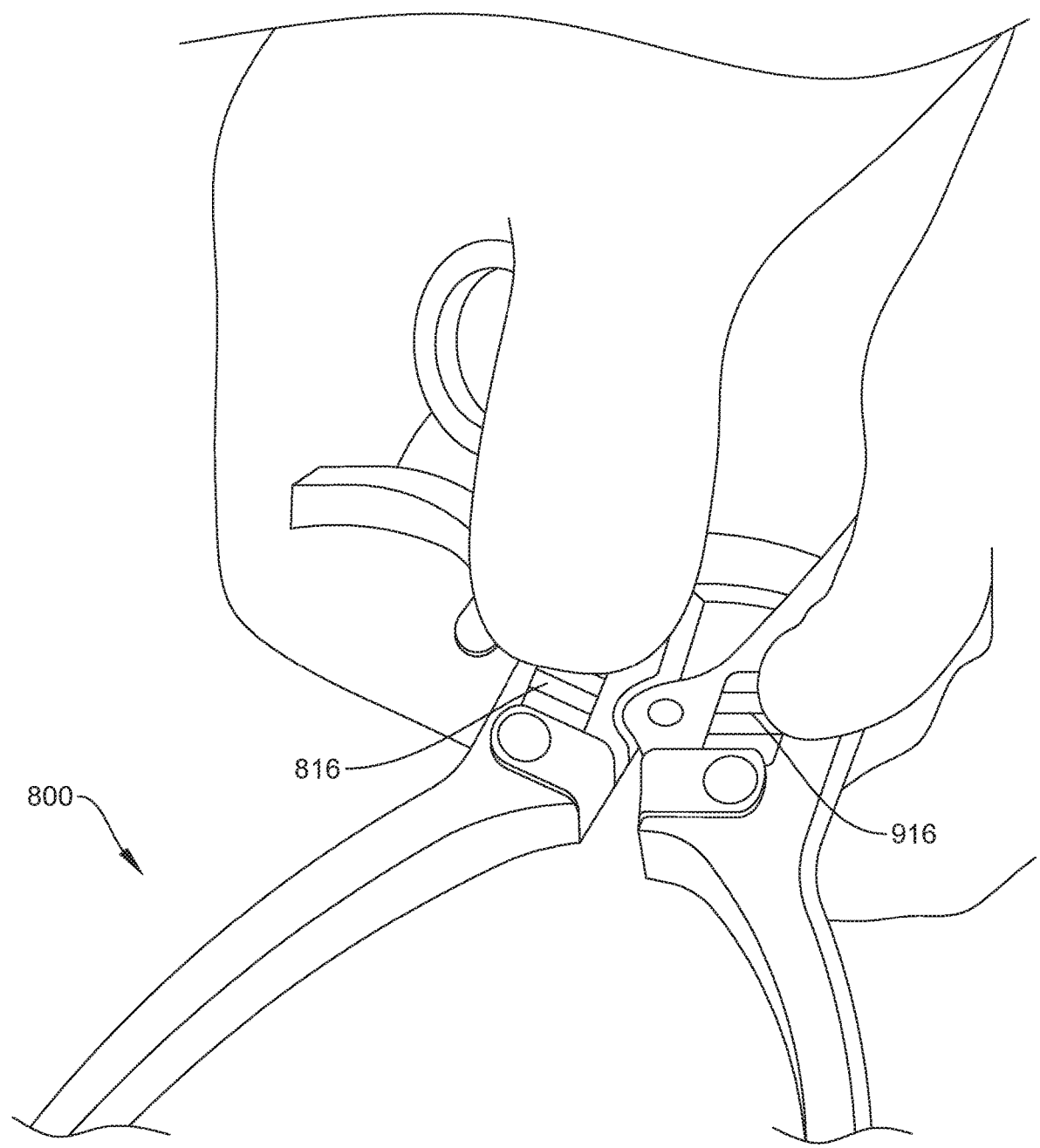
FIG. 50 is a perspective view of the components shown in FIG. 49.
Figure 51:
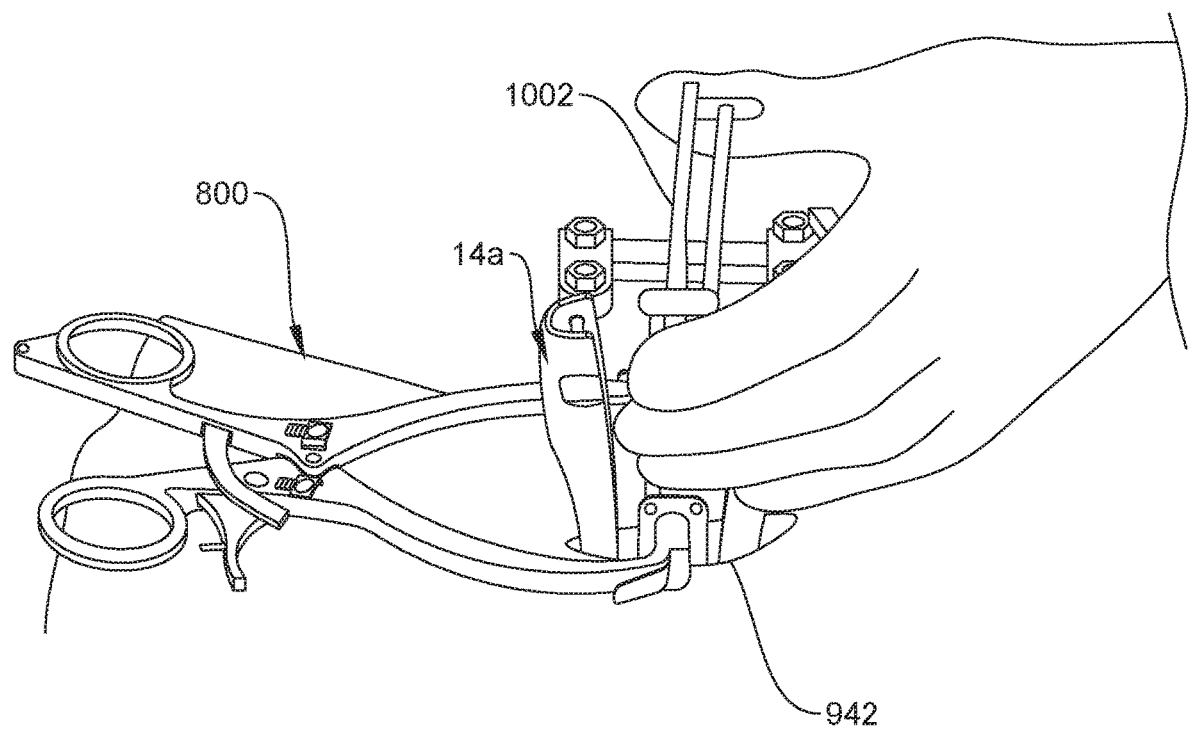
FIG. 51 is a perspective view of components of one embodiment of a surgical system disposed with a patient body.
Figure 52:
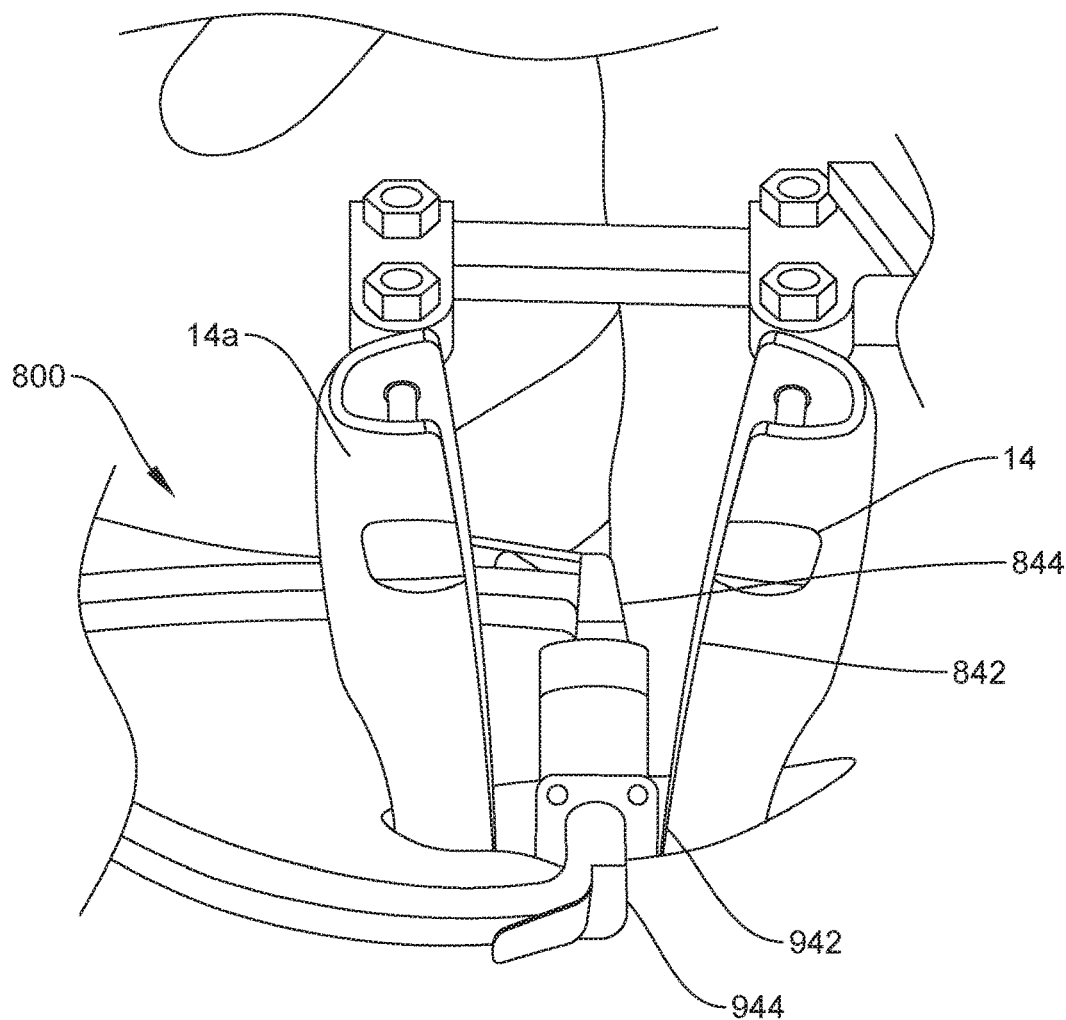
FIG. 52 is a break-away perspective view of the components shown in FIG. 51.

Latch 964 is disposed in an engaged position, as shown in FIG. 47. Retractor 800 is manipulated to retract tissue, as shown in FIG. 48. In some embodiments, key 966 is utilized for gradual tissue retraction, as shown in FIG. 49. One of blades 842, 942 can be articulated. Sliders 816, 916 are actuated for a controlled angulation of one of blades 842, 942 through an angular range, as shown in FIG. 50. In some embodiments, blade holders 1002 may be compressed to increase angulation, as shown in FIG. 51. Blade holders 1002 are removed. Retraction and/or angulation can be modified by manipulation of latch 964 and/or sliders 816, 916.

Figure 54:
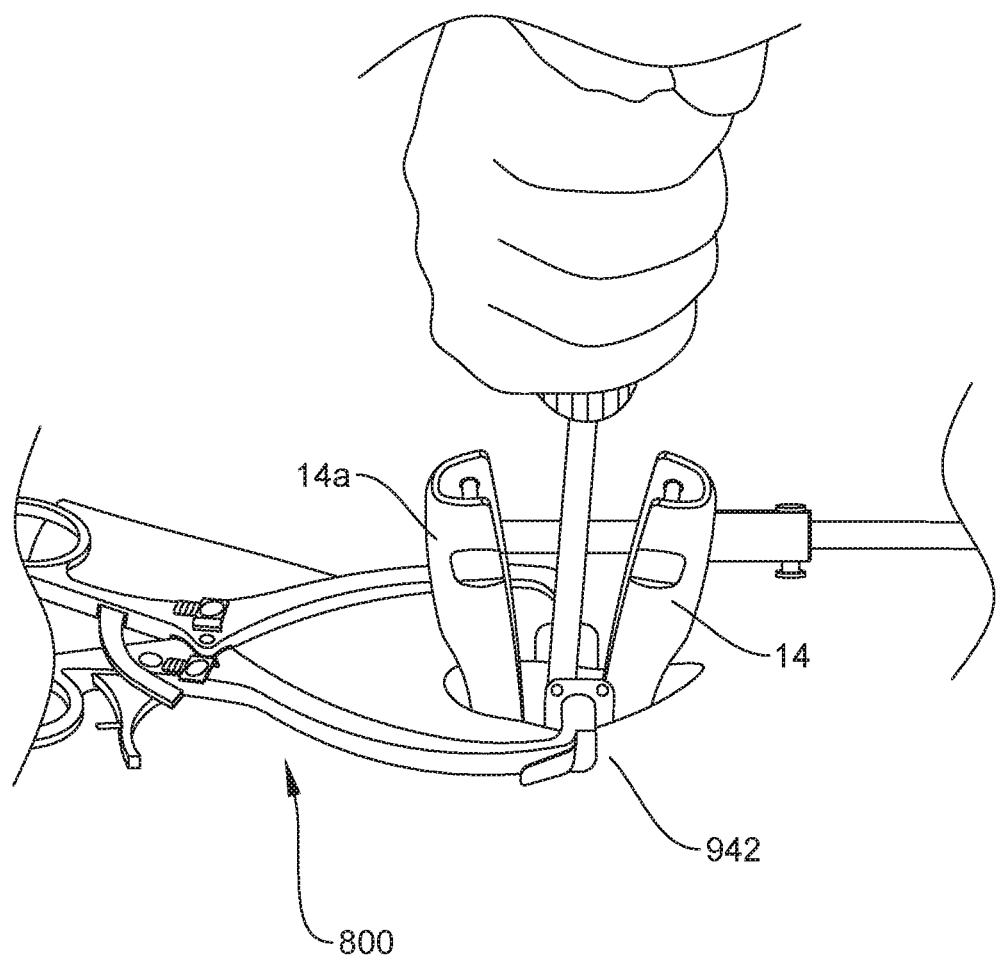
FIG. 54 is a perspective view of components of one embodiment of a surgical system disposed with a patient body.
Figure 55:
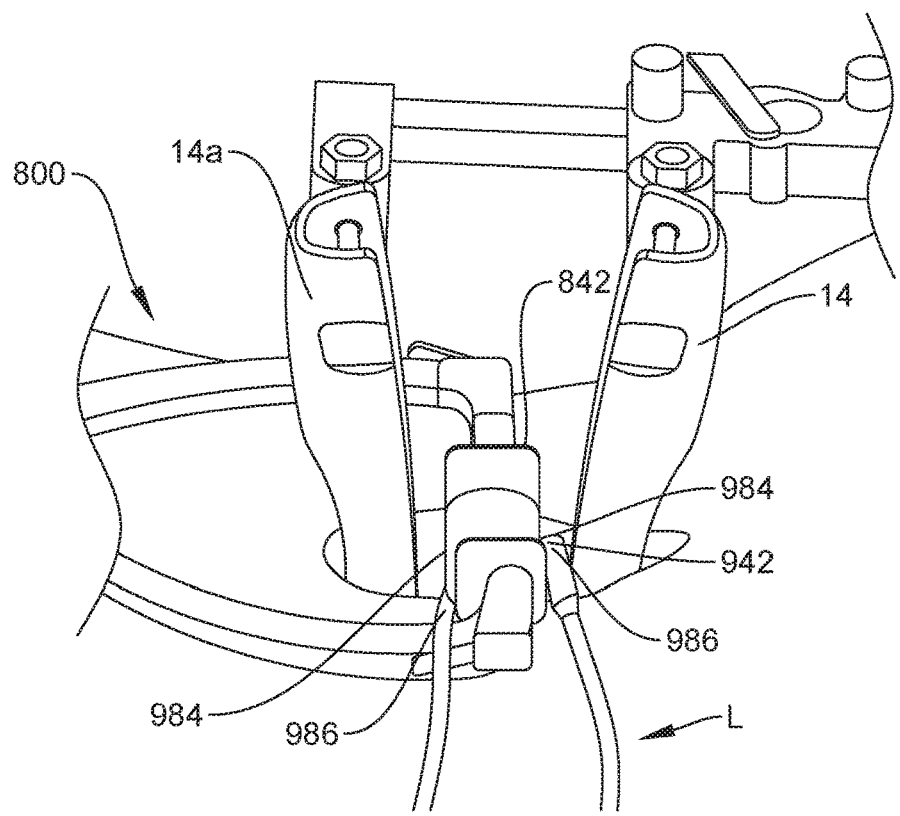
FIG. 55 is a perspective view of components of one embodiment of a surgical system disposed with a patient body.
Figure 56:
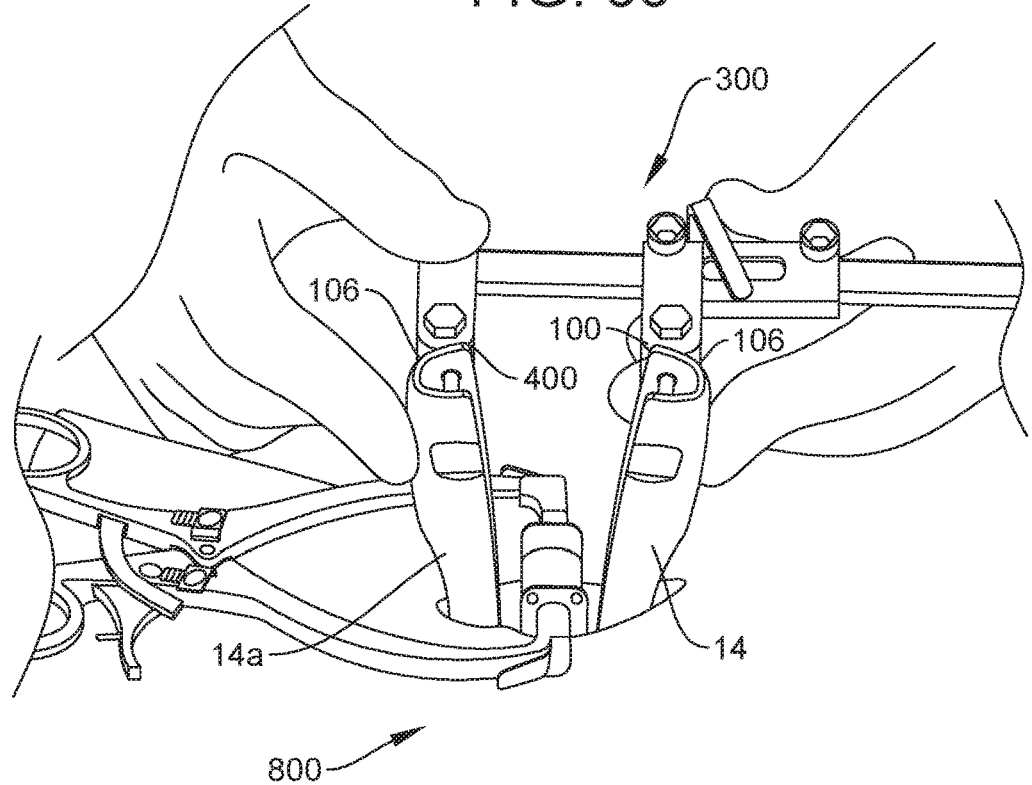
FIG. 56 is a perspective view of components of one embodiment of a surgical system disposed with a patient body.
Figure 57:
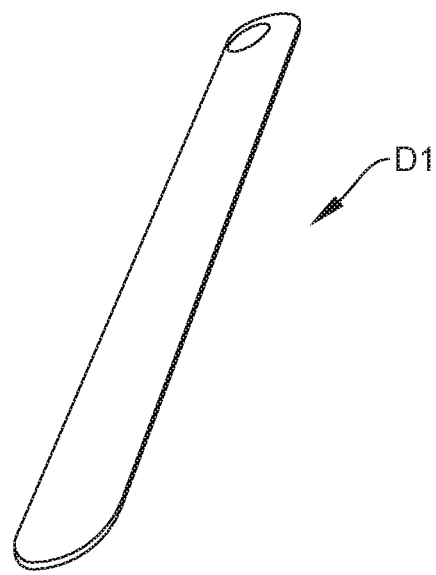
FIG. 57 is a perspective view of components of one embodiment of a surgical system in accordance with the principles of the present disclosure.

In some embodiments, retractor 800 includes a shorter blade 842 and/or blade 942 to resist and/or prevent damage to surrounding tissue during angulation. Blades 842, 942 can be changed in-situ at any time during the procedure by pressing buttons 844, 944 to release blades 842, 942 for connection with alternative and/or different sized blade 842, 942. Retractor 800 forms a passageway to facilitate insertion a spinal implant, such as, for example, an interbody spinal implant, as shown in FIG. 54. In some embodiments, a light source L, as described herein, is disposed with passageways 886, 986, as shown in FIG. 55, to provide illumination to the working channel. In some embodiments, to minimize instrumentation conflict with imaging or profile of distractor 300, distractor 300 may be hinged up or down while by manipulating adaptor 100 about pin hinge 106, as described herein and shown in FIG. 56.

In some embodiments, a rod inserter 500 is engaged with spinal rod 450, as described herein, to direct and/or guide spinal rod 450 through slots 70 and into receiver 18. In some embodiments, a driver 550 is utilized to engage a set screw 552 with bone fasteners 16, as described herein. In some embodiments, if segmental compression is required, set screws 552 are loosened and latch 320 is pivotable relative to arm 310 for disposal in a compression position, as described herein. Compressor/distractor 300 and implant supports 14, 14*a* are removed, as described herein.

Figure 58:
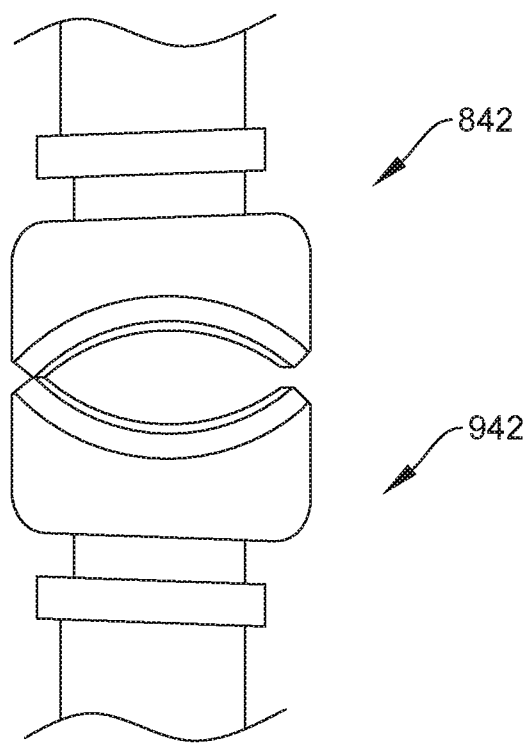
FIG. 58 is a plan view of components of one embodiment of a surgical system in accordance with the principles of the present disclosure.

In some embodiments, a dilator D1 includes a substantially oval cross-section configuration, such as, for example, a fish-eye configuration, as shown in FIG. 58. Blades 842, 942 are configured with a substantially oval shaped opening, as shown in FIG. 58, to facilitate a mating disposal of dilator D1.

Figure 59:
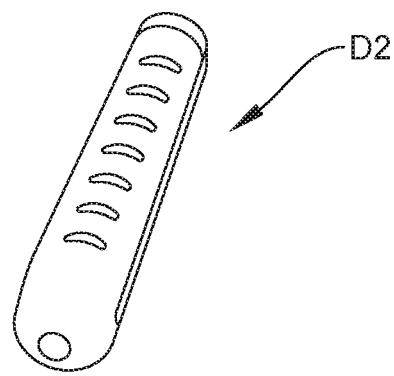
FIG. 59 is a perspective view of components of one embodiment of a surgical system in accordance with the principles of the present disclosure.
Figure 60:
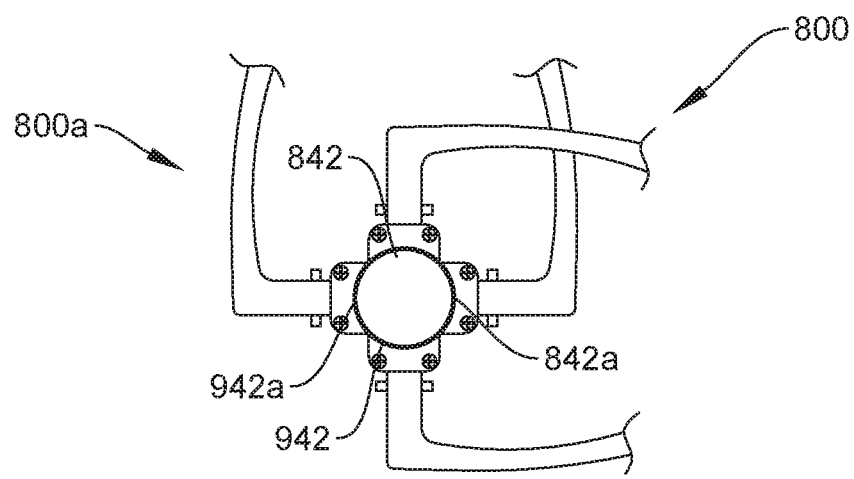
FIG. 60 is a plan view of components of one embodiment of a surgical system in accordance with the principles of the present disclosure.
Figure 61:
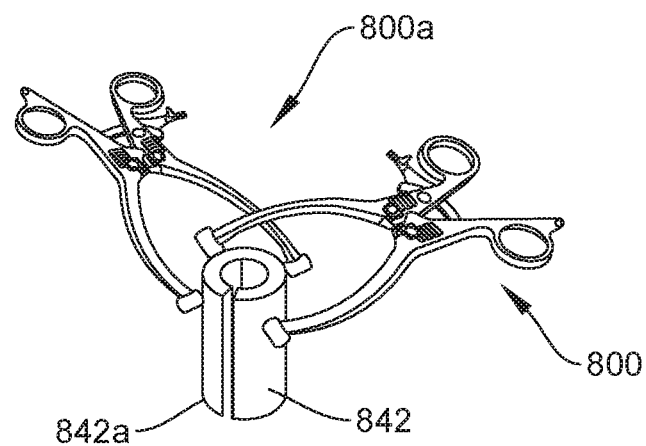
FIG. 61 is a perspective view of components of one embodiment of a surgical system in accordance with the principles of the present disclosure.

In some embodiments, a dilator D2 includes a substantially tubular cross-section configuration, as shown in FIG. 59, and surgical system 10 includes two sets of retractors 800, 800*a*, a shown in FIGS. 60 and 61. Blades 842, 842*a*, 942, 942*a* are configured with a substantially tubular shaped opening, as shown in FIG. 60, to facilitate a mating disposal of dilator D2.

In some embodiments, surgical system 10 includes one or a plurality of alternative surgical instruments, each configured for mating engagement in a quick release configuration with spinal constructs, as described herein. This configuration facilitates the interchangeability of the spinal constructs with the alternative surgical instruments. In some embodiments, surgical system 10 includes one or a plurality of alternative surgical instruments, such as, for example, inserters, extenders, reducers, spreaders, distractors, blades, retractors, clamps, forceps, elevators and drills, which may be alternatively sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including a first portion and a second portion, the second portion including an arm and a part, the part being connectable with a first blade such that the first blade is rotatable through a selected angular range relative to a proximal portion of the arm and through a selected angular range of about 0 to about 360 degrees relative to the part about a first central axis defined by the part of the first member;
   a second member including a first portion and a second portion, the second portion of the second member including an arm and a part, the part of the second member being connectable with a second blade such that the second blade is rotatable relative to the second member about a second central axis defined by the part of the second member; and
   the first portions being pivotably connected such that the blades are movable between a first configuration and a second configuration to space tissue adjacent a spine, wherein the second central axis being coaxial with the first central axis when in the first configuration.

2. A surgical instrument as recited in claim 1, wherein the first blade is rotatable through an angular range of about 0 through about 90 degrees relative to the arm.

3. A surgical instrument as recited in claim 1, wherein the part of the second member is connectable with the second blade such that the second blade is rotatable relative to a proximal portion of the arm of the second member through a selected angular range and through a selected angular range of about 0 to about 360 degrees relative to the part of the second member about a second central axis defined by the part of the second member.

4. A surgical instrument as recited in claim 1, wherein the part of the first member includes a socket and the first blade is releasably engageable with the socket via a pivot connection.

5. A surgical instrument as recited in claim 4, wherein the part of the first member includes a lock to releasably fix the first blade with the part of the first member.

6. A surgical instrument as recited in claim 1, wherein the first portion is pivotally connected with the second portion.

7. A surgical instrument as recited in claim 6, wherein the first portion and the second portion include a lock to releasably fix the first portion and the second portion.

8. A surgical instrument as recited in claim 6, wherein the lock is biased to a lock orientation.

9. A surgical instrument as recited in claim 6, wherein the lock includes a depressible spring button configured to release the second portion form the first portion.

10. A surgical instrument as recited in claim 1, wherein the first portions include a lock to selectively fix the first blade relative to the second blade.

11. A surgical system comprising:
    a first member including a first portion and a second portion, the second portion including an arm and a part transversley disposed on an end of the arm thereof, the part being connectable with a first blade such that the first blade is rotatable about a first central longitudinal axis defined by the part through a selected angular range of about 0 to about 360 degrees relative to the first central longitudinal axis, and about the transverse axis through a selected angular range, wherein the part of the first member includes a socket and the first blade is releasably engageable with the socket via a pivot connection; and
    a second member including a first portion and a second portion being connectable with a second blade, the second portion of the second member includes an arm and a part transversely disposed on an end of the arm thereof, defining a second central longitudinal axis, the part of the second member being connectable with the second blade such that the second blade is rotatable about the second central longitudinal axis through a selected angular range of about 0 to about 360 degrees relative to the second longitudinal axis;

the first portions being pivotably connected such that the blades are movable between a first configuration and a second configuration to define an opening and space tissue adjacent a spine, wherein the second central longitudinal axis is coaxial with the first central longitudinal axis in the first configuration.

12. A surgical system as recited in claim 11, further comprising a first implant support connected with a first fastener having a shaft fixed with the spine and a second implant support connected with a second fastener having a shaft fixed with the spine.

13. A surgical system as recited in claim 11, wherein the first portions comprise a handle and further comprising a driver engageable with the handle to selectively move the first blade relative to the second blade.

14. A surgical system as recited in claim 11, wherein the first portions comprise a handle connectable with a fixed surgical table.

15. A surgical system as recited in claim 11, further comprising a manipulation tool engageable with the first blade or the second blade.

16. A surgical system as recited in claim 11, wherein at least one of the blades define one or more channels configured for disposal of a light source apparatus, the one or more channels extending perpendicular to the first central longitudinal axis and the second central longitudinal axis.

17. A method for treating a spine, the method comprising the steps of:

engaging a first implant support with a first fastener having a shaft fixed with a spine;

engaging a second implant support with a second fastener having a shaft fixed with the spine, the implant support being connected with a first surgical instrument to distract and/or compress the spine;

disposing the first implant support relative to the second implant support in an axial orientation relative to the spine to define at least a portion of an opening and space tissue adjacent the spine; and moving a first member of a second surgical instrument relative to a second member of the second surgical instrument in a medial orientation relative to the spine to define at least a portion of the opening and space tissue adjacent the spine, wherein the first member includes a part, the part being connectable with a first blade such that the first blade is rotatable through a selected angular range of about 0 to about 360 degrees relative to the first member about a first central axis defined by the part, the second member including a part, the part of the second member being connectable with a second blade such that the second blade is rotatable through a selected angular range of about 0 to about 360 degrees relative to the second member about a second central axis defined by the part of the second member, the second central axis being coplanar with the first central axis while moving a first member of a second surgical instrument relative to a second member of the second surgical instrument.

18. A method as recited in claim 17, further comprising the step of manipulating the first blade or the second blade to a selected angular orientation.

19. A method as recited in claim 17, further comprising the step of disposing the blades such that the blades form a substantially oval cavity.

\* \* \* \* \*